(12) United States Patent
Deppermann et al.

(10) Patent No.: US 9,383,291 B2
(45) Date of Patent: *Jul. 5, 2016

(54) AUTOMATED CONTAMINATION-FREE SEED SAMPLER AND METHODS OF SAMPLING, TESTING AND BULKING SEEDS

(71) Applicant: Monsanto Technology LLC, St. Louis, MO (US)

(72) Inventors: Kevin L. Deppermann, St. Charles, MO (US); Jennifer Listello, O'Fallon, MO (US); Phillip Rahn, Ballwin, MO (US); Angela R. Cargill, St. Louis, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/685,033

(22) Filed: Apr. 13, 2015

(65) Prior Publication Data

US 2015/0355058 A1    Dec. 10, 2015

Related U.S. Application Data

(60) Continuation of application No. 14/032,850, filed on Sep. 20, 2013, now Pat. No. 9,027,278, which is a continuation of application No. 13/210,212, filed on Aug. 15, 2011, now Pat. No. 8,539,713, which is a (Continued)

(51) Int. Cl.
*G01N 1/04* (2006.01)
*A01C 1/00* (2006.01)

(Continued)

(52) U.S. Cl.
CPC .. *G01N 1/08* (2013.01); *A01C 1/00* (2013.01); *A01C 1/06* (2013.01); *G01N 1/04* (2013.01)

(58) Field of Classification Search
CPC ............. G01N 1/08; G01N 1/04; A01C 1/00; A01C 1/06
USPC .................................................... 47/58.1 SE
See application file for complete search history.

(56) References Cited

U.S. PATENT DOCUMENTS 2,756,903 A    7/1956   Kreidler
3,350,372 A    10/1967  Anspon et al.
(Continued)

FOREIGN PATENT DOCUMENTS

CL    1035-03    5/2003
CL    2189-05    8/2005
(Continued)

OTHER PUBLICATIONS

Anklam et al., Analytical methods for detection and determination of genetically modified organisms in agricultural crops and plant-derived food products. (Eur Food Res Technol. 214:3-26), Jan. 2002, 24 pages.
(Continued)

*Primary Examiner* — Monica Williams
(74) *Attorney, Agent, or Firm* — James E. Davis; Joseph A. Schaper; Harness, Dickey & Pierce, P.L.C.

(57) ABSTRACT

An automated seed sampler system includes an imaging device for obtaining images of seeds, an orienting device for orienting the seeds based on the images, and a sampling station for removing tissue from the oriented seeds. In some aspects, the system also includes a transport subsystem for supporting the oriented seeds and conveying the oriented seeds to the sampling station. A method for removing tissue from seeds includes imaging the seeds, orienting the seeds based on image information obtained from the seeds, and removing tissue from the oriented seeds. In some aspects, the method also includes transporting the oriented seeds in a transport subsystem to a sampling station for removing the tissue from the oriented seeds, and/or collecting the tissue removed from the oriented seeds so that a one-to-one correspondence exists between the tissue and the sampled seeds, and/or analyzing the tissue for characteristics indicative of genetic and/or chemical traits.

21 Claims, 19 Drawing Sheets

Related U.S. Application Data division of application No. 11/680,180, filed on Feb. 28, 2007, now Pat. No. 7,998,669.

(60) Provisional application No. 60/778,830, filed on Mar. 2, 2006.

(51) Int. Cl.
*G01N 1/08* (2006.01)
*A01C 1/06* (2006.01)

(56) References Cited

U.S. PATENT DOCUMENTS

| | | |
|---|---|---|
| 3,530,372 A | 9/1970 | Laukien |
| 3,642,128 A | 2/1972 | Westwood et al. |
| 3,852,914 A | 12/1974 | Levengood |
| 3,861,788 A | 1/1975 | Webster |
| 4,037,970 A | 7/1977 | Webster et al. |
| 4,040,747 A | 8/1977 | Webster |
| 4,260,262 A | 4/1981 | Webster |
| 4,305,130 A | 12/1981 | Kelley |
| 4,375,854 A | 3/1983 | Hedel |
| 4,480,765 A | 11/1984 | Tonus |
| 4,654,592 A | 3/1987 | Zens |
| 4,734,584 A | 3/1988 | Rosenthal |
| 4,752,689 A | 6/1988 | Satake |
| 4,818,380 A | 4/1989 | Azegami et al. |
| 4,884,696 A | 12/1989 | Peleg |
| 4,931,061 A | 6/1990 | Young |
| 4,946,046 A | 8/1990 | Affleck et al. |
| 5,051,699 A | 9/1991 | Hanawa |
| 5,132,538 A | 7/1992 | Norris |
| 5,221,518 A | 6/1993 | Mills |
| 5,245,188 A | 9/1993 | Satake et al. |
| 5,253,302 A | 10/1993 | Massen |
| 5,412,220 A | 5/1995 | Moore |
| 5,475,221 A | 12/1995 | Wang |
| 5,533,145 A | 7/1996 | Shofner et al. |
| 5,590,791 A | 1/1997 | Gschweitl |
| 5,668,374 A | 9/1997 | DiFoggio et al. |
| 5,669,511 A | 9/1997 | Satake et al. |
| 5,733,592 A | 3/1998 | Wettstein et al. |
| 5,751,421 A | 5/1998 | Wright et al. |
| 5,764,819 A | 6/1998 | Orr et al. |
| 5,833,947 A | 11/1998 | Rocklage |
| 5,836,438 A | 11/1998 | Jung |
| 5,837,458 A | 11/1998 | Minshull et al. |
| 5,864,984 A | 2/1999 | McNertney |
| 5,918,977 A | 7/1999 | Borggaard et al. |
| 5,991,025 A | 11/1999 | Wright et al. |
| 6,100,526 A | 8/2000 | Mayes |
| 6,150,158 A | 11/2000 | Bhide et al. |
| 6,237,286 B1 | 5/2001 | Williams |
| 6,266,864 B1 | 7/2001 | Barber |
| 6,307,123 B1 | 10/2001 | Kriz et al. |
| 6,397,678 B1 | 6/2002 | Popper |
| 6,537,826 B1 | 3/2003 | Horigane |
| 6,646,264 B1 | 11/2003 | Modiano et al. |
| 6,705,827 B2 | 3/2004 | Keller et al. |
| 6,706,989 B2 | 3/2004 | Hunter et al. |
| 6,782,991 B2 | 8/2004 | Johansson |
| 6,879,389 B2 | 4/2005 | Meyer et al. |
| 6,947,144 B2 | 9/2005 | Kim et al. |
| 6,959,617 B2 | 11/2005 | Deppermann |
| 7,044,306 B2 | 5/2006 | Deppermann |
| 7,067,834 B2 | 6/2006 | Horigane et al. |
| 7,367,155 B2 | 5/2008 | Kotyk et al. |
| 7,502,113 B2 | 3/2009 | Deppermann et al. |
| 7,591,101 B2 | 9/2009 | Deppermann |
| 7,600,642 B2 | 10/2009 | Deppermann |
| 7,611,842 B2 | 11/2009 | Deppermann et al. |
| 7,703,238 B2 | 4/2010 | Deppermann et al. |
| 7,767,883 B2 | 8/2010 | Deppermann et al. |
| 7,830,516 B2 | 11/2010 | Deppermann et al. |
| 7,832,143 B2 | 11/2010 | Deppermann et al. |
| 7,849,632 B2 | 12/2010 | Deppermann et al. |
| 7,877,926 B2 | 2/2011 | Deppermann |
| 7,941,969 B2 | 5/2011 | Deppermann et al. |
| 7,998,669 B2 | 8/2011 | Deppermann et al. |
| 8,028,469 B2 | 10/2011 | Deppermann et al. |
| 8,071,845 B2 | 12/2011 | Deppermann et al. |
| 8,245,439 B2 | 8/2012 | Deppermann et al. |
| 8,312,672 B2 | 11/2012 | Deppermann et al. |
| 8,443,545 B2 | 5/2013 | Deppermann et al. |
| 8,539,713 B2 | 9/2013 | Deppermann et al. |
| 8,561,346 B2 | 10/2013 | Deppermann et al. |
| 8,959,833 B2 | 2/2015 | Deppermann et al. |
| 8,997,398 B2 | 4/2015 | Deppermann et al. |
| 9,003,696 B2 | 4/2015 | Deppermann et al. |
| 9,027,278 B2 | 5/2015 | Deppermann et al. |
| 2001/0013486 A1 | 8/2001 | Yamakawa |
| 2001/0014750 A1 | 8/2001 | Ulrich et al. |
| 2002/0070150 A1 | 6/2002 | Keller et al. |
| 2002/0144458 A1 | 10/2002 | Hunter et al. |
| 2003/0142852 A1 | 7/2003 | Lu et al. |
| 2004/0074822 A1 | 4/2004 | Horigane et al. |
| 2004/0141641 A1 | 7/2004 | McDonald et al. |
| 2004/0160607 A1 | 8/2004 | Lin et al. |
| 2005/0082207 A1 | 4/2005 | Deppermann |
| 2005/0097021 A1 | 5/2005 | Behr et al. |
| 2005/0114918 A1 | 5/2005 | Hirahara et al. |
| 2006/0042527 A1 | 3/2006 | Deppermann |
| 2006/0042528 A1 | 3/2006 | Deppermann |
| 2006/0046244 A1 | 3/2006 | Deppermann |
| 2006/0046264 A1 | 3/2006 | Deppermann et al. |
| 2006/0048247 A1 | 3/2006 | Deppermann |
| 2006/0048248 A1 | 3/2006 | Deppermann |
| 2006/0112628 A1 | 6/2006 | Kotyk et al. |
| 2007/0048872 A1 | 3/2007 | Deppermann et al. |
| 2007/0204366 A1 | 8/2007 | Deppermann et al. |
| 2007/0207485 A1 | 9/2007 | Deppermann et al. |
| 2007/0240242 A1 | 10/2007 | Modiano et al. |
| 2008/0000815 A1 | 1/2008 | Deppermann |
| 2008/0113367 A1 | 5/2008 | Becker et al. |
| 2008/0131254 A1 | 6/2008 | Cope et al. |
| 2008/0131924 A1 | 6/2008 | Cope et al. |
| 2008/0317279 A1 | 12/2008 | Deppermann et al. |
| 2009/0032441 A1 | 2/2009 | Corak et al. |
| 2009/0155878 A1 | 6/2009 | Becker et al. |
| 2010/0263087 A1 | 10/2010 | Deppermann et al. |
| 2010/0299790 A1 | 11/2010 | Deppermann et al. |
| 2011/0081716 A1 | 4/2011 | Deppermann |
| 2011/0129836 A1 | 6/2011 | Deppermann et al. |
| 2011/0217700 A1 | 9/2011 | Deppermann et al. |
| 2011/0296930 A1 | 12/2011 | Deppermann et al. |
| 2012/0021411 A1 | 1/2012 | Deppermann et al. |
| 2012/0117865 A1 | 5/2012 | Deppermann et al. |
| 2012/0180386 A1 | 7/2012 | Deppermann et al. |
| 2012/0228199 A1 | 9/2012 | Modiano et al. |
| 2012/0288854 A1 | 11/2012 | Deppermann et al. |
| 2013/0167257 A1 | 6/2013 | Deppermann et al. |
| 2013/0244321 A1 | 9/2013 | Deppermann |
| 2013/0260366 A1 | 10/2013 | Deppermann et al. |
| 2015/0164011 A1 | 6/2015 | Deppermann et al. |
| 2015/0241322 A1 | 8/2015 | Deppermann et al. |
| 2015/0355205 A1 | 12/2015 | Deppermann et al. |

FOREIGN PATENT DOCUMENTS

| | | |
|---|---|---|
| CL | 2190-05 | 8/2005 |
| CL | 573-07 | 3/2007 |
| CN | 2510248 | 9/2002 |
| DE | 198 45 883 A1 | 5/1999 |
| DE | 10 2004 06376 | 7/2006 |
| EP | 0 127 313 | 7/1989 |
| EP | 0 636 310 | 2/1995 |
| EP | 0 730 164 | 9/1996 |
| EP | 0 750 188 | 12/1996 |
| EP | 0 511 184 | 6/1998 |
| EP | 0 539 537 | 12/2000 |
| EP | 1 126 268 A1 | 8/2001 |
| EP | 1 401 589 | 1/2003 |
| EP | 1 786 261 | 5/2007 |
| EP | 1 991 043 | 5/2010 |

(56) References Cited

FOREIGN PATENT DOCUMENTS

| | | |
|---|---|---|
| EP | 2 279 658 | 2/2011 |
| FR | 2549963 | 1/1985 |
| GB | 1151988 A | 5/1969 |
| GB | 1355612 | 6/1974 |
| GB | 1408458 | 10/1975 |
| GB | 1471076 A | 4/1977 |
| JP | 406284806 A | 10/1994 |
| JP | 10-319106 | 12/1998 |
| JP | 2000055910 A | 2/2000 |
| RU | 2126618 C1 | 2/1999 |
| RU | 2267766 C1 | 1/2006 |
| SU | 1446521 | 12/1989 |
| SU | 1805835 A3 | 3/1993 |
| WO | WO 96/24830 | 8/1996 |
| WO | WO 97/00887 | 1/1997 |
| WO | WO 98/14046 A | 4/1998 |
| WO | WO 98/44140 | 10/1998 |
| WO | WO 99/40419 | 8/1999 |
| WO | WO 99/41383 | 8/1999 |
| WO | WO 99/58959 | 11/1999 |
| WO | WO 00/52990 | 9/2000 |
| WO | WO 00/71993 | 11/2000 |
| WO | WO 01/022043 | 3/2001 |
| WO | WO 01/44828 | 6/2001 |
| WO | WO 01/89288 | 11/2001 |
| WO | WO 02/16090 | 2/2002 |
| WO | WO 02/048687 | 6/2002 |
| WO | WO 02/059586 | 8/2002 |
| WO | WO 02/071040 | 9/2002 |
| WO | WO 03/100381 | 12/2003 |
| WO | WO 2005/031367 | 5/2005 |
| WO | WO 2006/026466 | 3/2006 |
| WO | WO 2006/026467 | 3/2006 |
| WO | WO 2007/025250 | 3/2007 |
| WO | WO 2008/150798 | 12/2008 |
| WO | WO 2012/012411 | 1/2012 |

OTHER PUBLICATIONS

Archibald et al., "Development of Short-Wavelength Near-Infrared Spectral Imaging for Grain Color Classification," SPIE vol. 3543, pp. 189-198 (1998).
Arumuganathan, K. & Earle, E.D., *Estimation of Nuclear DNA Content of Plants by Flow Cytometry*, Plant Molecular Biology Reporter 9(3):229-241 (1991).
Bauman et al., Inheritance of Variations in Oil Content of Individual Corn (*Zea mays* L.) Kernels, Crop Science, 5:137-138 (1965).
Benito et al., Rapid identification of Triticeae genotypes from single seeds using the polymerase chain reaction, Plant Molecular Biology 21:181-183, 1993, 3 pages.
Bor-Yaw Lin, Ploidy Barrier to Endosperm Development in Maize (Genetics 107:103-115), May 1984, 13 pages.
Chenault et al., A Non-destructive Seed Sampling Method for PCR-based Analyses in Marker Assisted Selection and Transgene Screening, Peanut Science, 34:38-43 (2007).
Churchill, F., *William Johannsen and the Genotype Concept*, Journal of the History of Biology, 7(1):5-30 (1974).
Concibido, V.C. et al., *Introgression of a quantitative trait locus for yield from Glycine soja into commercial soybean cultivars*, Theor. Appl. Genet. 106:575-582 (2003).
Daun et al., "Comparison of Three Whole Seed Near-Infrared Analyzers for Measuring Quality Components of Canola Seed", *JAOCS*, 71(10):1063-1068 (1994).
Delwiche, "Single Wheat Kernel Analysis by Near-Infrared Transmittance: Protein Content," Analytical Techniques and Instrumentation, *JAOCS*, 72(1):11-16 (1995).
Dowell et al., "Automated Single Wheat Kernel Quality Measurement Using Near-Infrared Reflectance," *ASAE Annual International Meeting*, paper No. 973022 (1997).
Dowell et al., "Automated Color Classification of Single Wheat Kernels Using Visible and Near-Infrared Reflectance," *Cereal Chem* 75(1):142-144 (1998).

Dowell, "An Intelligent Automated System for Determining Peanut Quality," *IEEE International Workshop on Intelligent Robots and Sytems, IROS*, pp. 237-241 (1990).
Dr. Jolanta Soos, "Industrial Process Monitoring Requires Rugged AOTF Tools", Laser Focus World, Aug. 1994.
Eder, J. & Chalyk, S., *In vivo haploid induction in maize*, Theor. Appl. Genet., 104:703-708 (2002).
Frisch, M. et al., *Comparison of Selection Strategies for Marker-Assisted Backcrossing of a Gene*, Crop Science 39:1295-1301 (1999).
Gambhir et al. "Simultaneous Determination of Moisture and Oil Content in Oilseeds by Pulsed Nuclear Magnetic Resonance," *JAOCS*, 62(1):103-108 (1985).
Gao et al., Development of a seed DNA-based genotyping system for marker-assisted selection in maize, Moi Breeding, 22:477-494 (2008).
Gao et al., Revisiting the Hetero-Fertilization Phenomenon in Maize, PLoS ONE, vol. 6, Issue 1, Jan. 2011, 7 pages.
Gillaspie, Jr., Sensitive Method for Testing Peanut Seed Lots for Peanut Stripe and Peanut Mottle Viruses by Immunocapture-Reverse Transcription-Polymerase Chain Reaction, Plant Disease, May 2000, pp. 559-561.
Groos, C. et al., *Study of the relationship between pre-harvest sprouting and grain color by quantitative trait loci analysis in a whitexred grain bread-wheat cross*, Theor. Appl. Genet. 104:39-47 (2002).
Halloin et al. "Proton Magnetic Resonance Imaging of Lipid in Pecan Embryos," *JAOCS*, 70(12):1259-1262 (1993).
He, L. & Wang, K., *A 384-Well Microtiter-Plate-Based Template Preparation and Sequencing Method*, PCR Cloning Protocols 411-416 (2nd. ed., Humana Press 2002).
Heil et al. "Magnetic Resonance Imaging and Modeling of Water Up-take into Dry Beans," *Lebensm-Wiss u-Technol*, 25:280-285 (1992).
Horigane et al., *Two-dimensional analysis of kernels using a new sample preparation method*, Chemistry and Biology, 41 (6):398-402, Jun. 25, 2003 (Published in Japanese—an English language translation is included).
Horigane, A. et al., *Evaluation of Color Characteristics of Cross-Sectioned Wheat Kernels*, Food Science & Technology Research 9(4):327-331 (2003).
Jones D A L M Barber et al., "An analysis of seed development in *Pisum sativum* L. XVI. Assessing variation for fatty acid content by use of a non-destructive technique for single-seed analysis", Plant Breeding, vol. 114, No. 1, 1995, pp. 81-83.
Jousse et al., Rapid, cost-effective screening of flax genotypes to identify desirable fatty acid compositions, Electronic Journal of Plant Breeding, 1(6):1396-1404 (2010).
Kamiya et al., Rapid DNA Extraction Method from Soybean Seeds, Breeding Science 53:277-279 (2003).
Kang et al., A Rapid DNA Extraction Method for RFLP and PCR Analysis from a Single Dry Seed, Plant Molecular Biology Reporter, 16:1-9 (1998).
Kato, A., *Chromosome doubling of haploid maize seedlings using nitrous oxide gas at the flower primordial stage*, Plant Breeding 121:370-377 (2002).
Kisha, T.J. et al., *Genetic Diversity among Soybean Plant Introductions and North American Germplasm*, Crop Science 38:1669-1680 (1998).
Kotyk et al., High-throughput determination of oil content in corn kernels using nuclear magnetic resonance imaging, Journal of the American Oil Chemists' Society, vol. 82, No. 12, Dec. 2005, pp. 855-862.
Kramer et al., *Transgenic Avidin Maize is Resistant to Storage Insect Pests*, Nature Biotechnology, vol. 18, Jun. 2000, pp. 670-674.
Kristensen, H. and Aastrup, S., A non-destructive screening method for proanthocyanidin-free barley mutants, Carlesberg Res. Commun. 51 (1986) 509-513.
Krysan, Breakthrough Technologies, Ice-Cap. A High-Throughput Method for Capturing Plant Tissue Samples for Genotype Analysis, Plant Physiology, Jul. 2004 vol. 135, pp. 1162-1169.
Lakshminarayana et al. "Spatial distribution of oil in groundnut and sunflower seeds by nuclear magnetic resonance imaging," *J. Biosci* 17(1):87-93 (1992).

(56) References Cited

OTHER PUBLICATIONS

Li et al., Molecular Mapping Genes Conditioning Reduced Palmitic Acid Content in N87-2122-4 Soybean (Crop Science 42:373-378), 2002, 6 pages.
Lipman et al., *Tolerance of Liquid-Air Temperature by Seeds of Higher Plants for Sixty Days*, Plant Physiology 392-394 (1934).
MacNamara et al., "Multiplex sample NMR: an approach to high-throughput NMR using a parallel coil probe," *Analytica Chimica Acta*, 397:9-16 (1999).
Manabe et al., Segregation distortion through female gametophates in interspecific hybrids of tetraploid wheat as revealed by RAPD analysis (Hereditas 131: 47-53), Oct. 1999, 7 pages.
Massie, et al. "Spectral Reflectance and Transmittance Properties of Grain in the Visible and near Infrared", Transactions of the ASAE, Winter Meeting of the American Society of Agricultural Engineers, pp. 598-600 (1965).
McEntyre et al., "Comparison of Water Absorption Patterns in Two Barley Cultivars, Using Magnetic Resonance Imaging," *Cereal Chem.*, 75(6):792-795 (1998).
McGinty et al. "A System for Automatic Weight Determination of Individual Grain Kernels: Principles and Evaluation," *Cereal Chem.* 19(5):196-199 (1974).
Meru et al., A non-destructive genotyping system from a single seed for marker-assisted selection in watermelon, GMR Genetics and Molecular Research 12(1):702-709 (2013).
Notice of Opposition to European Patent EP 1869961 (Application No. EP07016960.2) as filed by Syngenta Crop Protection AG on Oct. 25, 2012, and related filings, 52 pages.
Notice of Opposition to European Patent EP 1991043 (Application No. 07757774.0) as filed by Syngenta Crop Protection AG, 29 pages, Feb. 18, 2011.
Preliminary Opinion of Opposition Division relating to Opposition of European Patent EP 1869961 (Application No. EP07016960.2), Dec. 20, 2013, 11 pages.
Notice of Third Party Observations filed in European Patent EP 1869961 (Application No. EP07016960.2) Dec. 14, 2012, 11 pages.
Notice of Opposition to European Patent EP 2279657 (Application No. EP10184375.3) as filed by Syngenta Crop Protection AG on Dec. 6, 2013, 21 pages.
Orman, et al. "Comparison of Near-Infrared Spectroscopy Calibration Methods for the Prediction of Protein, Oil, and Starch in Maize Grain," *J. Agric. Food Chem.* 39:883-886 (1991).
P.A. Hailey, "The Role Of Nir Spectroscopy in the Measurement of Pharmaceutical Manufacture", http://wwwbrimrose.com/hailey.html; (Jan. 2, 2002).
Paige et al. "Apparatus for Automatic Measurement of Kernel Weight, Length, and Thickness," *Crop Sci.* 31:1314-1318 (1991).
Pioneer Hi-Bred International, Inc., Downloadable Photos—Laser-Assisted Seed Selection, http://www.pioneer.com/web/site/portal/menuiteam.b9e99dcb8e2cfd8ecfe6d10093a0/, printed as of Nov. 25, 2008, 4 pages.
Petition for Inter Partes Review of U.S. Pat. No. 8,312,672 as filed by E.I. du Pont de Nemours and Company on Jan. 8, 2014, 71 pages (and 34 Exhibits).
Petition for Inter Partes Review of U.S. Pat. No. 8,071,845, as filed by E.I. du Pont de Nemours and Company on Jan. 8, 2014, 60 pages (and 25 Exhibits).
Petition for Inter Partes Review of U.S. Pat. No. 7,832,143, as filed by E.I. du Pont de Nemours and Company on Jan. 8, 2014, 70 pages (and 24 Exhibits).
Petition for Inter Partes Review of U.S. Pat. No. 8,245,439, as filed by E.I. du Pont de Nemours and Company on Jan. 8, 2014, 69 pages (and 27 Exhibits).
Petition for Inter Partes Review of U.S. Pat. No. 8,028,469, as filed by E.I. du Pont de Nemours and Company on Jan. 8, 2014, 51 pages (and 25 Exhibits).
R.K. Downey, Genetic Control of Fatty Acid Biosynthesis in Rapeseed (*Brassica napus* L.) (AOCS 41:475-478), 1964, 4 pages.
R.K.Downey, Methods of Breeding for Oil Quality in Rape (Canadian Journal of Plant Science 43:271-275), Jul., 1963, 7 pages.
Rapid identification of organic contaminants in pretreated waste water using AOTF near-IR spectrometry, ISA 1995 Meeting Proceedings, pp. 87-95 (1995).
Robutti, "Maize Kernel Hardness Estimation in Breeding by Near-Infrared Transmission Analysis," *Cereal Chem* 72(6): 632-636 (1995).
Rubel et al. "Simultaneous Determination of Oil and Water Contents in Different Oilseeds by Pulsed Nuclear Magnetic Resonance," *JAOCS* 71(10):1057-1062 (1994).
Saito et al. "Application of Magnetic Resonance Imaging to Non-Destructive Void Detection in Watermelon," *Cryogenics* 36(12):1027-1031 (1996).
Sander et al., "System for Automatic Weight Determination of Individual Grain Kernels," *Transactions of the ASAE*, pp. 1146-1147 (1973).
Sangtong, V. et al., *Serial Extraction of Endosperm Drillings (SEED)—A Method for Detecting Transgenes and Proteins in Single Viable Maize Kernels*, Plant Molecular Biology Reporter, 19:151-158 (2001).
Seed Meister Luminar 3076, Brimrose Corporation of America, Baltimore, MD, http://www.brimrose.com/seed_meister.html; (Jan. 3, 2002).
Siebenmorgen et al. "A Data Acquisition/Control System for Individual Kernel and Thin-Layer Grain Drying Research" *Am. Soc. Of Agri. Engrs., Univ. Of Ark., 1991 Int'l Summer Meeting*, Paper 91/3042, pp. 1-16 (1991).
Smith et al., *Genetic Purity and Testing Technologies for Seed Quality: A Company Perspective*, Seed Science Research, 1998, vol. 8, pp. 285-293.
Song et al., "Non-invasive Measurement of Moisture Distribution in Individual Wheat Kernels by Magnetic Resonance Imaging," *SPIE*, 2345:414-422 (1994).
Tanksley et al., Seed Banks and Molecular Maps: Unlocking Genetic Potential from the Wild (Science 277:1063-1066) Aug., 1997, 5 pages.
Varshney et al., Plant Biotechnology and Molecular Markers (Kluwer Academic Publishers; Print ISBN: 1-4020-1911-4; Edited by P.S. Srivastava, Alka Narula, Sheela Srivastava) (Chapter 20), Apr., 2004, 42 pages.
Von Post et al., A High-Throughput DNA Extraction Method for Barley Seed, Euphytica 130: 255-260, 2003.
Wright, H., *Commercial Hybrid Seed Production*, Hybridization of Crop Plants 161-176 (1980).
Yoshida et al., "An automatic sequential single-seed weighing system: variation in soybean seed weight," *J. Fac. Agr. Hokkido Univ.* 61(2):225-232 (1982).
Zeile, W.L. et al., "A Rapid Non-Destructive Technique for Fatty Acid Determination in Individual Peanut Seed" Peanut Science (1993) 20:9-11 (3 pages).

AUTOMATED CONTAMINATION-FREE SEED SAMPLER AND METHODS OF SAMPLING, TESTING AND BULKING SEEDS

CROSS-REFERENCE TO RELATED APPLICATIONS

This application is a continuation of U.S. patent application Ser. No. 14/032,850, filed Sep. 20, 2013, which is a continuation of U.S. patent application Ser. No. 13/210,212, filed Aug. 15, 2011 (now U.S. Pat. No. 8,539,713), which is a divisional of U.S. patent application Ser. No. 11/680,180, filed Feb. 28, 2007 (now U.S. Pat. No. 7,998,669), which claims priority to and the benefit of U.S. Provisional Application No. 60/778,830, filed Mar. 2, 2006. The disclosures of each of these applications are incorporated herein by reference in their entireties.

FIELD

This disclosure relates to systems and methods for taking samples from biological materials such as seeds.

BACKGROUND

The statements in this section merely provide background information related to the present disclosure and may not constitute prior art.

In plant development and improvement, genetic improvements are made in the plant, either through selective breeding or genetic manipulation, and when a desirable improvement is achieved, a commercial quantity is developed by planting and harvesting seeds over several generations. Not all seeds express the desired traits, and thus these seeds need to be culled from the population. To speed up the process of bulking up the population, statistical samples are taken and tested to cull seeds from the population that do not adequately express the desired trait. However, this statistical sampling necessarily allows some seeds without the desirable trait to remain in the population, and also can inadvertently exclude some seeds with the desirable trait from the desired population.

U.S. patent application Ser. No. 11/213,430 (filed Aug. 26, 2005); U.S. patent application Ser. No. 11/213,431 (filed Aug. 26, 2005); U.S. patent application Ser. No. 11/213,432 (filed Aug. 26, 2005); U.S. patent application Ser. No. 11/213,434 (filed Aug. 26, 2005); and U.S. patent application Ser. No. 11/213,435 (filed Aug. 26, 2005), which are incorporated herein by reference in their entirety, disclose apparatus and systems for the automated sampling of seeds as well as methods of sampling, testing and bulking seeds.

However, at least some known automated sampling and testing systems allow for various types of contamination to taint collected samples and skew results. Therefore, there exists a need for the automated sampling of seeds in a substantially contamination-free manner.

SUMMARY

The present disclosure relates to systems and methods of non-destructively sampling material from seeds. The methods are particularly adapted for automation, which permits greater sampling than was previously practical. With automated, non-destructive sampling permitted by at least some of the embodiments of this disclosure, it is possible to test every seed in the population, and cull those seeds that do not express a desired trait. This greatly speeds up the process of bulking a given seed population, and can result in an improved final population.

Various embodiments of the present disclosure facilitate the testing of most or all of the seeds in a population before planting, so that time and resources are not wasted in growing plants without the desired traits. Further, various embodiments allow for the automated sampling of seeds in a contamination-free manner, thereby substantially eliminating cross-over between samples.

In various embodiments, the present disclosure provides an automated seed sampler system that includes a milling station for removing at least a portion of seed coat material from a seed and a sampling station for extracting a sample of seed material from the seed where the seed coat has been removed. A seed transport subsystem conveys the seed between the milling station and the sampling station and a seed deposit subsystem conveys the seed from the seed transport subsystem to a selected well in a seed tray after the seed has been sampled.

In various other embodiments, the present disclosure provides an automated seed sampler system that includes a milling station for removing at least a portion of seed coat material from a seed and a sampling station for extracting a sample of seed material from the seed where the seed coat has been removed. A sample collection and transport subsystem captures the extracted sample in a collection tube mounted on a collection tube placement device of the sample collection and transport subsystem. Additionally, a sample deposit subsystem conveys the sample from the sample collection and transport subsystem to a selected well in a sample tray.

In yet other various embodiments, the present disclosure provides a method of extracting sample material from a seed for testing. The method includes loading a seed in a seed holder of an automated seed sampler system and removing at least a portion of seed coat material from the seed at a milling station of the seed sampler system. A sample of seed material is then extracted from the seed where the seed coat has been removed at a sampling station of the seed sampler system. The sampled seed is then conveyed to a selected well in a seed tray using a seed deposit subsystem of the seed sampler system. The extracted sample is coincidentally conveyed to a selected well in a sample tray using a sample deposit subsystem of the seed sampler system. The deposited sample can then be tested for at least one desired seed characteristic.

In still other embodiments, the present disclosure provides an automated system for sequentially removing sample material from a plurality of seeds while leaving the viability of the seeds intact. The system includes a milling station for sequentially removing at least a portion of seed coat material from each seed and a sampling station for sequentially extracting a sample of seed material from each seed where the seed coat has been removed from the respective seed. A seed transport subsystem conveys the seeds between the milling station and the sampling station and a seed deposit subsystem sequentially conveys each seed from the seed transport subsystem to a selected one of a plurality of wells in a selected one of a plurality of seed trays. The system additionally includes a sample collection and transport subsystem for sequentially capturing the extracted sample of each seed in a corresponding collection tube mounted on one of a plurality of collection tube placement devices. The system further includes a sample deposit subsystem for sequentially conveying each sample from the sample collection and transport subsystem to a selected one of a plurality of wells in a selected one of a plurality of sample trays.

In other embodiments of the present disclosure, a method for removing tissue samples from seeds generally includes orienting seeds in a desired orientation, transporting the oriented seeds to a sampling station, and removing tissue samples from the oriented seeds at the sampling station.

In other embodiments of the present disclosure, an automated method for removing a tissue sample from a seed generally includes isolating an individual seed from a plurality of seeds, orienting the isolated seed using an actuator, and removing a tissue sample from the oriented seed. Here, the actuator is configured to position the seed in a desired orientation.

In other embodiments of the present disclosure, a method for removing tissue samples from seeds generally includes orienting multiple seeds together in a seed transport and removing tissue samples from the oriented seeds while the oriented seeds are in the seed transport.

The systems and methods of this disclosure facilitate the automated, non-destructive sampling of seeds in a substantially contamination-free manner. They permit the testing and sorting of large volumes of seeds, thereby facilitating the bulking up of seed populations with desirable traits. These and other features and advantages will be in part apparent, and in part pointed out hereinafter.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

Corresponding reference numerals indicate corresponding parts throughout the several views of the drawings.

DETAILED DESCRIPTION

Figure 1:
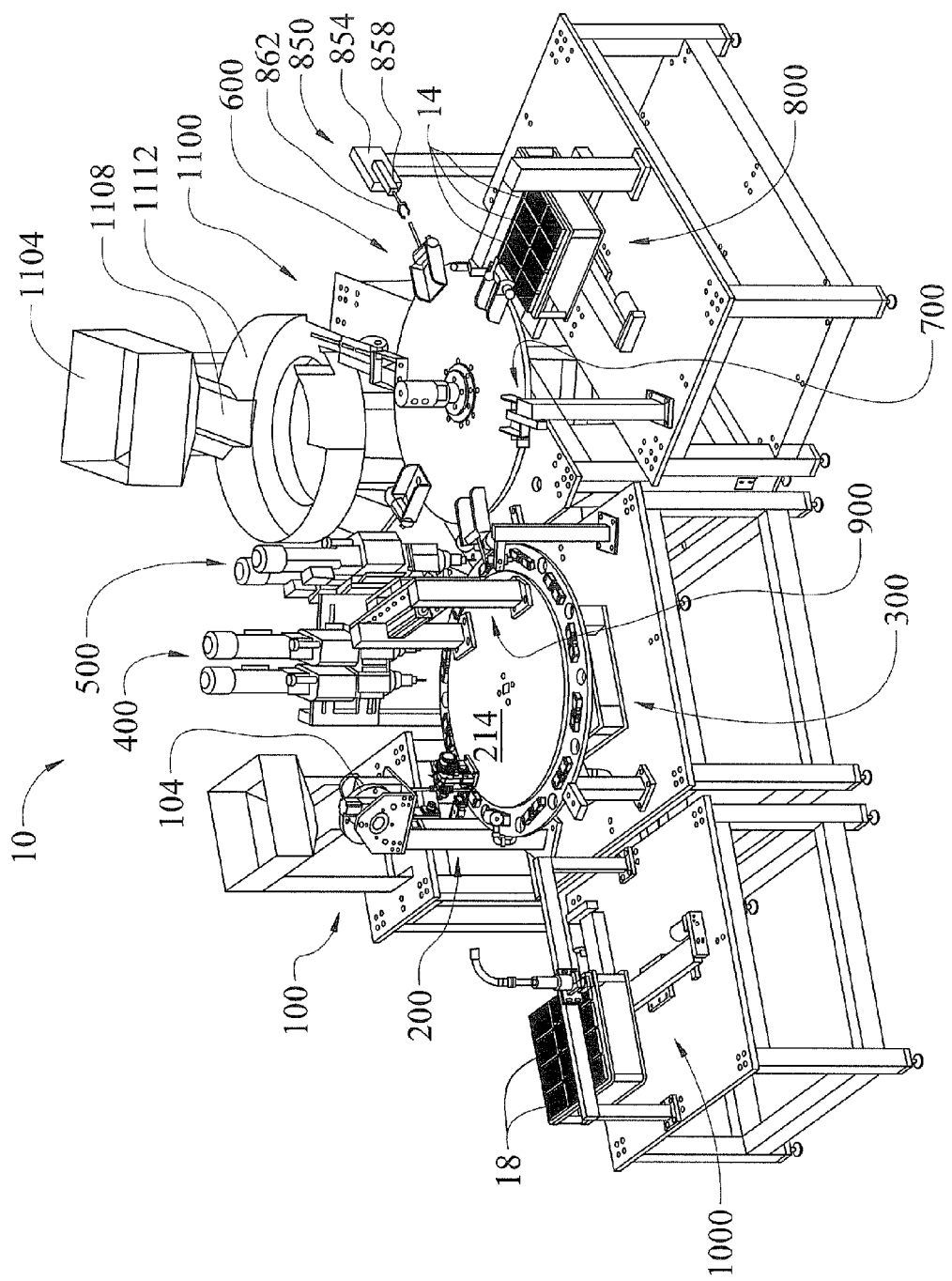
FIG. 1 is a perspective view of a seed sampler system in accordance with various embodiments of the present disclosure.

The following description is merely exemplary in nature and is in no way intended to limit the present teachings, application, or uses. Throughout this specification, like reference numerals will be used to refer to like elements.

FIG. 1 illustrates an automated seed sampler system 10, in accordance with various embodiments of the present disclosure. Generally, the seed sampler system 10 includes a seed loading station 100, a seed orientation system 200, a seed transport subsystem 300, a milling station 400, a sampling station 500, a sample collection and transport subsystem 600, a liquid delivery subsystem 700, a sample deposit subsystem 800, a seed treatment station 900 and a seed deposit subsystem 1000.

The seed sampler system 10 is structured and operable to isolate a seed from a seed bin 104 of the seed loading station 100, orient the seed at the seed orientation station 200 and transfer the seed to the milling station 400, via the transport subsystem 300. The seed sampler system 10 is further structured and operable to remove a portion of the seed coat material at the milling station 400, transfer the seed to the sampling station 500, via the seed transport subsystem 300, where sample material is extracted from the seed at the point where the seed coat material has been removed. The seed sampler system 10 is still further structured and operable to convey the extracted sample to the sample deposit subsystem 800, via the sample transport subsystem 700, and deposit the extracted sample into a sample tray 14 located on the sample deposit subsystem 800. In various embodiments, the sample material is collected in a disposable sample tube and delivered to the sample tray 14 using liquid, as described further below. Further yet, the seed sampler system 10 is structured and operable to treat, e.g., apply a protective coating to, the exposed portion of the seed at the seed treatment station 900 and convey the seed to the seed deposit subsystem 1000, where the seed is deposited into a seed tray 18 located on a platform of the seed deposit subsystem 1000.

It should be understood that the seed sampler system 10, as shown and described herein, includes various stationary braces, beams, platforms, pedestals, stands, etc. to which various components, devices, mechanisms, systems, subsystems, assemblies and sub-assemblies described herein are coupled, connected and/or mounted. Although such braces, beams, platforms, pedestals, stands, etc. are necessary to the construction of the seed sampler system 10, description of their placement, orientation and interconnections are not necessary for one skilled in the art to easily and fully comprehend the structure, function and operation of the seed sampler system 10. Particularly, such braces, beams, platforms, pedestals, stands, etc. are clearly illustrated throughout the figures and, as such, their placement, orientation and interconnections are easily understood by one skilled in the art. Therefore, for simplicity, such braces, beams, platforms, pedestals, stands, etc. will be referred to herein merely as system support structures, absent further description of their placement, orientation and interconnections.

Figure 2:
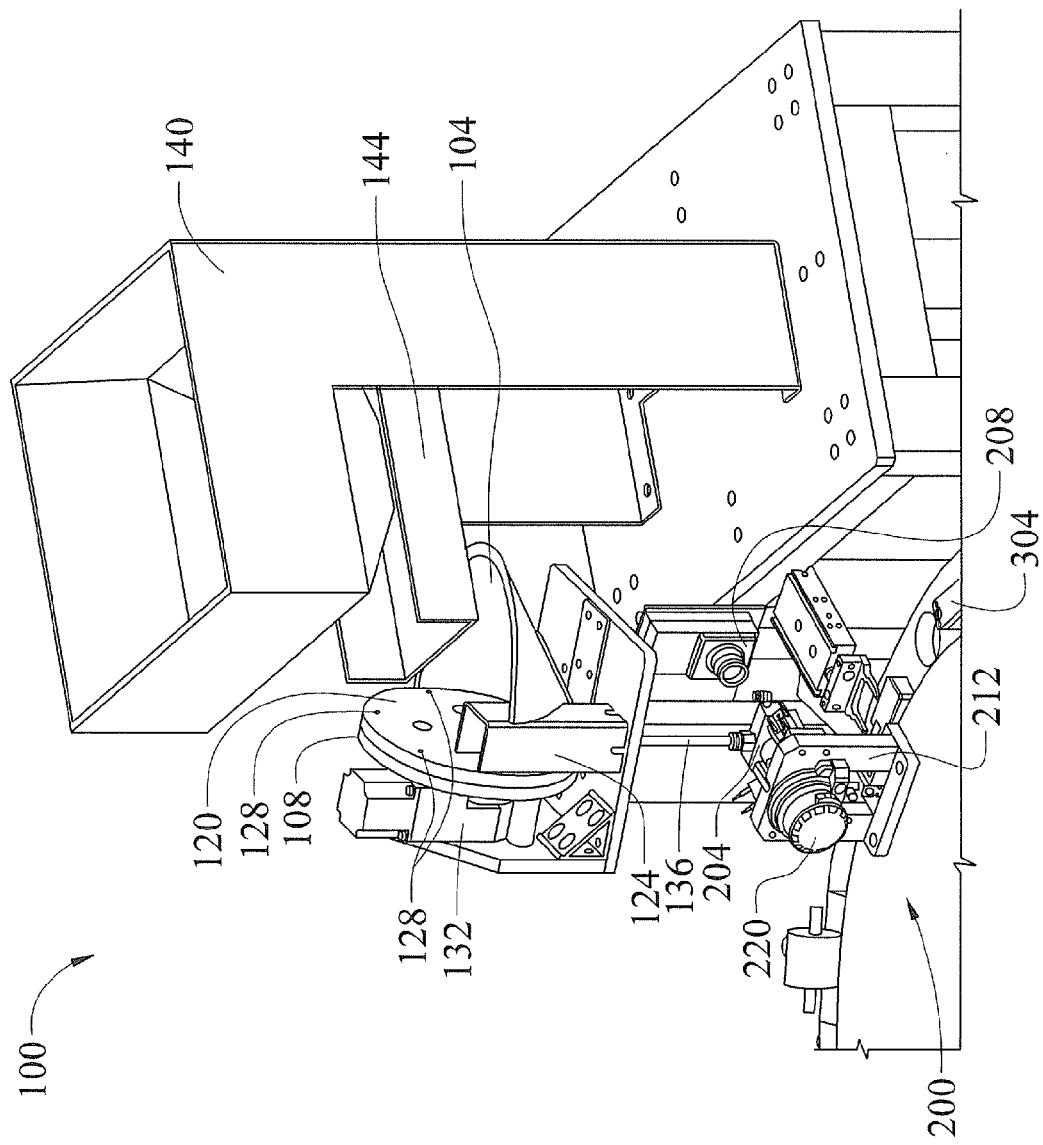
FIG. 2 is an enlarged perspective view of a seed loading station of the seed sampler system shown in FIG. 1, in accordance with various embodiments of the present disclosure.
Figure 3:
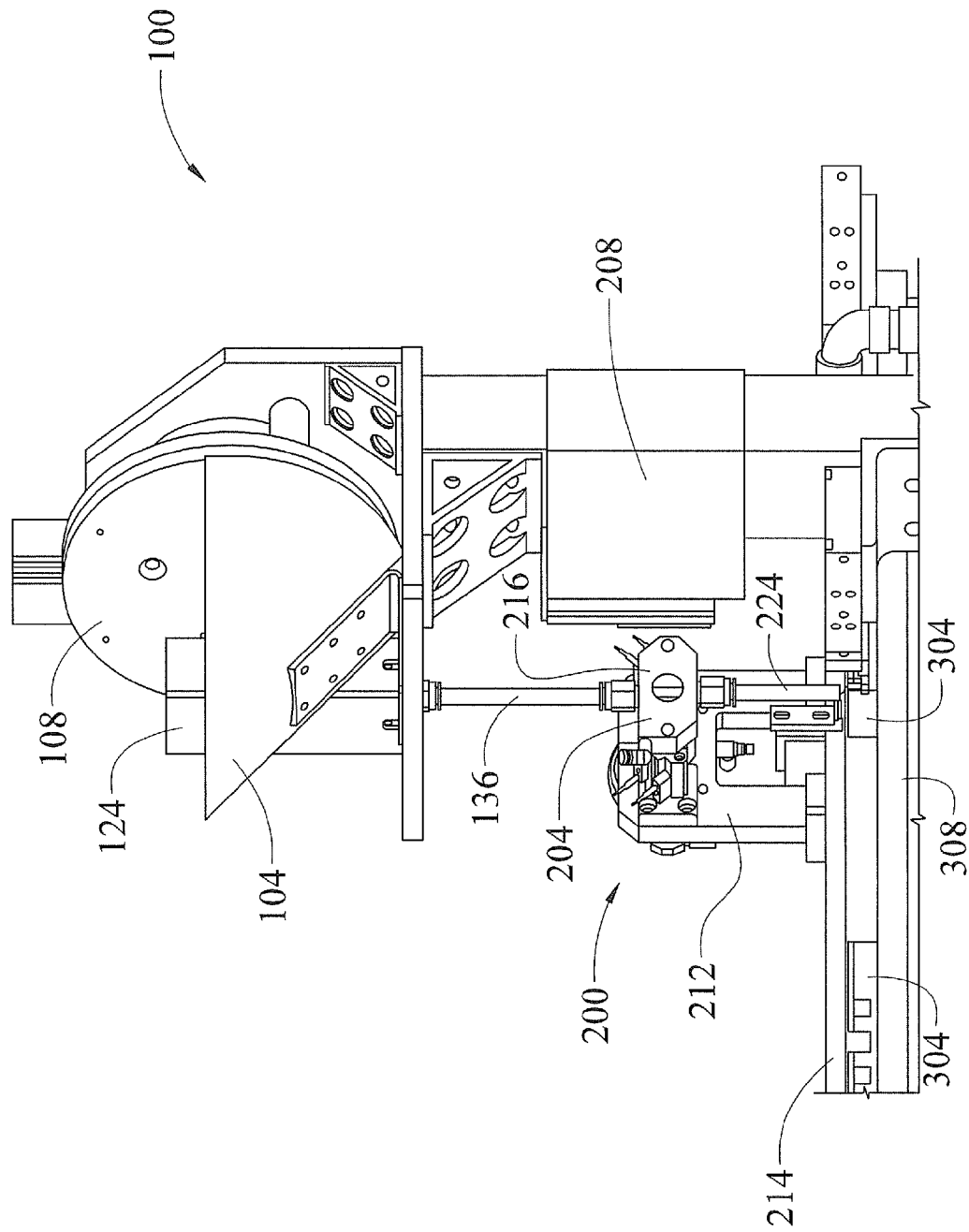
FIG. 3 is an enlarged perspective view of a seed orientation system of the seed sampler system shown in FIG. 1, in accordance with various embodiments of the present disclosure.

Referring now to FIGS. 2 and 3, in various embodiments, the seed loading station includes the seed bin 104 and a separating wheel 108. The separating wheel 108 is mounted for rotation in a vertical plane such that a portion of the separating wheel 108 extends into an interior reservoir of the seed bin 104. Another portion of the separating wheel 108 extends outside of the seed bin 104 such that a face 120 of the separating wheel 108 is positioned adjacent a seed collector 124. The seed separating wheel 108 includes a plurality of spaced apart recessed ports 128 that extend through the face 120 and are communicatively coupled to a vacuum system (not shown) such that a vacuum can be provided at each of the recessed ports 128.

To initiate operation of the seed sampler system 10, seeds to be sampled and tested are placed in the seed bin 104 interior reservoir and a vacuum is provided to at least some of the recessed ports 128, e.g., the recessed ports 128 in the face 120 of the portion of the separating wheel 108 extending into the interior reservoir of the seed bin 104. The seed separating wheel 108 is then incrementally rotated, via an indexing motor 132, such that recessed ports 128 sequentially rotate through the interior reservoir of the seed bin 104, out of the seed bin 104, and past seed collector 124 before re-entering the interior reservoir of the seed bin 104. As the separating wheel incrementally rotates and the recessed ports 128 incrementally pass through the seed bin 104 interior reservoir, individual seeds are picked up and held at each recessed port 128 by the vacuum provided at the respective recessed ports 128. As the separating wheel 108 incrementally rotates, the seeds are carried out of the seed bin 104 to the seed collector 124 where each seed is removed from the face 120 of the separating wheel 108. After each seed is removed from the separating wheel 108, the seed is funneled to a loading station transfer tube 136. The seed is then passed through the loading station transfer tube 136, via gravity, vacuum or forced air, into a seed imaging fixture 204 of the seed orientation system 200. The loading station transfer tube 136 is sized to have an inside diameter that will only allow the seed to pass through the loading station transfer tube 136 in a longitudinal orientation. That is, the seed can only pass through the loading station transfer tube 136 in either a tip-up or tip-down orientation and the inside diameter will not allow the seed to tumble or flip as it passes through the loading station transfer tube 136.

In various embodiments, the seed collector 124 includes a wiper (not shown) that physically dislodges each seed from the respective recessed port 128 as the separating wheel 108 incrementally rotates past the seed collector 124. Thereafter, the dislodged seed passes through the loading station transfer tube 136 to the imaging fixture 204. Alternatively, in various other embodiments, each seed can be released from respective recessed port 128 by temporarily terminating the vacuum at each individual recessed port 128 as the individual recessed port 128 is positioned adjacent the seed collector 124. Thereafter, the dislodged seed is transferred to the imaging fixture 204, via the loading station transfer tube 136. In still other embodiments, each seed can be blown from the respective recessed port 128 by temporarily providing forced air at each individual recessed port 128 as the individual recessed port 128 is positioned adjacent the seed collector 124. Thereafter, the dislodged seed is transferred to the imaging fixture 204, via the loading station transfer tube 136.

Additionally, in various embodiments the seed loading station 100 can include a bulk seed hopper 140 having a shaped surface and a vibrating feeder mechanism 144. Large amounts of seed can be placed in the hopper 140 where the seed is funneled onto the vibrating feed mechanism 144. The vibrating feeder mechanism 144 can be controlled to meter seeds into the seed bin 104 where the seeds are separated and transferred to the imaging fixture 204 of the seed orienting system 200, as described above.

Figure 4:
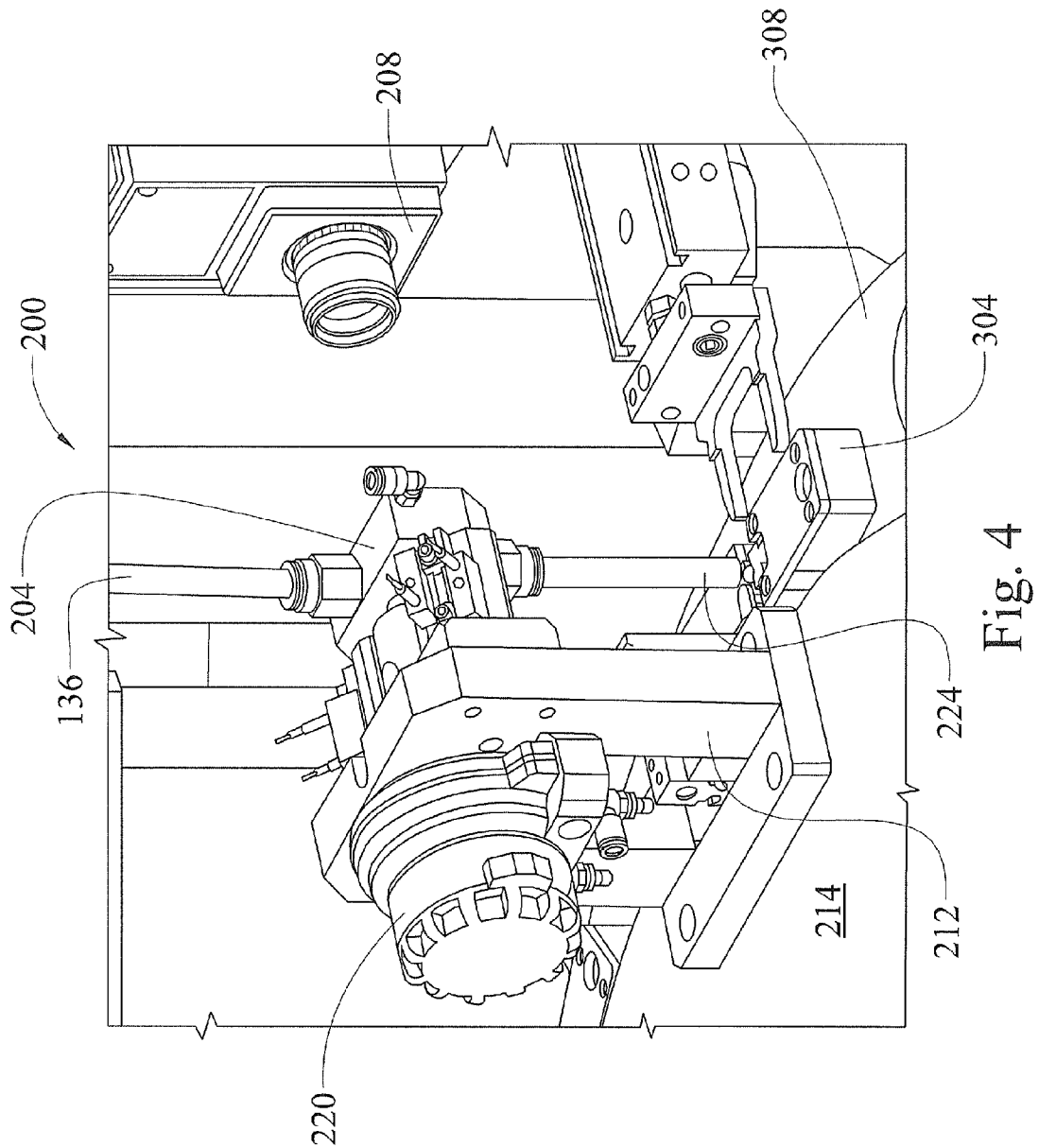
FIG. 4 is a side elevation view of the seed orientation system shown in FIG. 3, in accordance with various embodiments of the present disclosure.

Referring now to FIGS. 3 and 4, the seed orientation system 200 comprises the seed imaging fixture 204, an imaging device 208, and a seed orienting device 212 mounted to a stationary center platform 214 of the seed sampler system 10. The seed imaging fixture 204 includes a window 216 and an internal seed orientation area that is visible through the window 216. The orienting device 212 includes a flipper actuator 220 operable to rotate the seed while the seed is suspended in the seed orientation area. The imaging fixture 204 is connected to an end of the loading station transfer tube 136 and the imaging device 208 is mounted to a system support structure adjacent the imaging fixture such that the imaging device 208 is positioned to view a seed suspended in the seed orientation area through the window 216.

When a seed is transferred to the imaging fixture 204, via the loading station transfer tube 136, the seed is suspended within the seed orientation area, adjacent the window 216, and viewed by the imaging device 208 through the window 216. In various other embodiments, the seed is levitated within the seed orientation area using air provided through an orientation system transfer tube 224 connected to the bottom of the imaging fixture 204, opposite the loading station transfer tube 136. Or, in various embodiments, the seed can be physically held within the seed orientation area using any suitable mechanical holding means.

As the seed is suspended adjacent the window 216, an image of the seed within the imaging fixture 204 is collected by the imaging device 208. The imaging device 208 can be any imaging device suitable for collecting images through the window 216 of the seeds suspended within the seed orientation area. For example, in various embodiments, the imaging device 208 comprises a high speed, high resolution digital camera, such as a disruptive visual technology (DVT) machine vision camera. The image is communicated to a computer based system controller (not shown), where an orientation of the seed, i.e., tip-up or tip-down, is determined. In a various embodiments, the seed imaging device 208 additionally locates a centroid of the seed and identifies the farthest point from the centroid as the tip.

If the seed is determined to be tip-down, the seed is conveyed in the tip-down orientation, via the orientation system transfer tube 224, to one of a plurality of seed holders 304. If the seed is determined to be tip-up, the flipper actuator 220 is commanded by the system controller to rotate the seed 180° to place the seed in the tip-down orientation. For example, the flipper actuator 220 can be air-operated such that air is used to rotate the seed until the tip-down orientation is detected by the imaging device 208. Or, the flipper actuator can be a mechanical actuator that rotates the seed held by a suitable mechanical holding device to place the seed in the tip-down orientation. Once in the tip-down orientation, the seed is conveyed in the tip-down orientation, via the orientation system transfer tube 224, to one of the seed holders 304. Orienting the seeds in the tip-down position minimizes the impact to the seed's viability when a sample is removed from the seed, as described below. In various embodiments, the seeds are conveyed via the orientation system transfer tube 224 utilizing gravity, i.e., the seeds fall from the imaging fixture 204, through the transfer tube 224 and into one of the seed holders 304. Additionally, each seed is maintained in the proper orientation, i.e., tip-down, during conveyance to the respective seed holder 304 by providing the orientation system transfer tube 224 with an inside diameter sized such that the seeds cannot rotate to the tip-up position.

As used herein, the system controller can be a single computer based system, or a plurality of subsystems networked together to coordinate the simultaneous operations of the seed sample system 10, described herein. For example, the system controller can include a plurality of controller subsystems, e.g., a controller subsystem for each station described herein. Each controller subsystem could include one or more processors or microprocessors that communicate with various seed sampler system sensors, devices, mechanisms, motors, tools, etc., and are networked together with a main computer system to cooperatively operate all the stations, systems and subsystems of the seed sampler system 10. Or alternatively, the system controller could comprise a single computer communicatively connected to all the various sensors, devices, mechanisms, motors, tools, etc., to cooperatively operate all the stations, systems and subsystems of the seed sampler system 10.

The seed holders 304 are mounted to, and equally spaced around a perimeter area of, a motorized turntable 308 of the seed transport subsystem 300. The orientation system transfer tube 224 is connected at a first end to the seed imaging fixture 204 such that a second end of the orientation system transfer tube 224 is positioned a specific distance above a perimeter portion of the turntable 308. More particularly, the second end of the orientation system transfer tube 224 is positioned above the turntable 308 a distance sufficient to allow the seed holders 304 to pass under the orientation system transfer tube second end. However, the second end of the orientation system transfer tube 224 is also positioned above the turntable 308 such that there is only a small amount of clearance between the second end and the holders 304. Therefore, each seed will remain in the tip-down orientation as it transitions from the orientation system transfer tube 224 to one of the seed holders 304.

Figure 5:
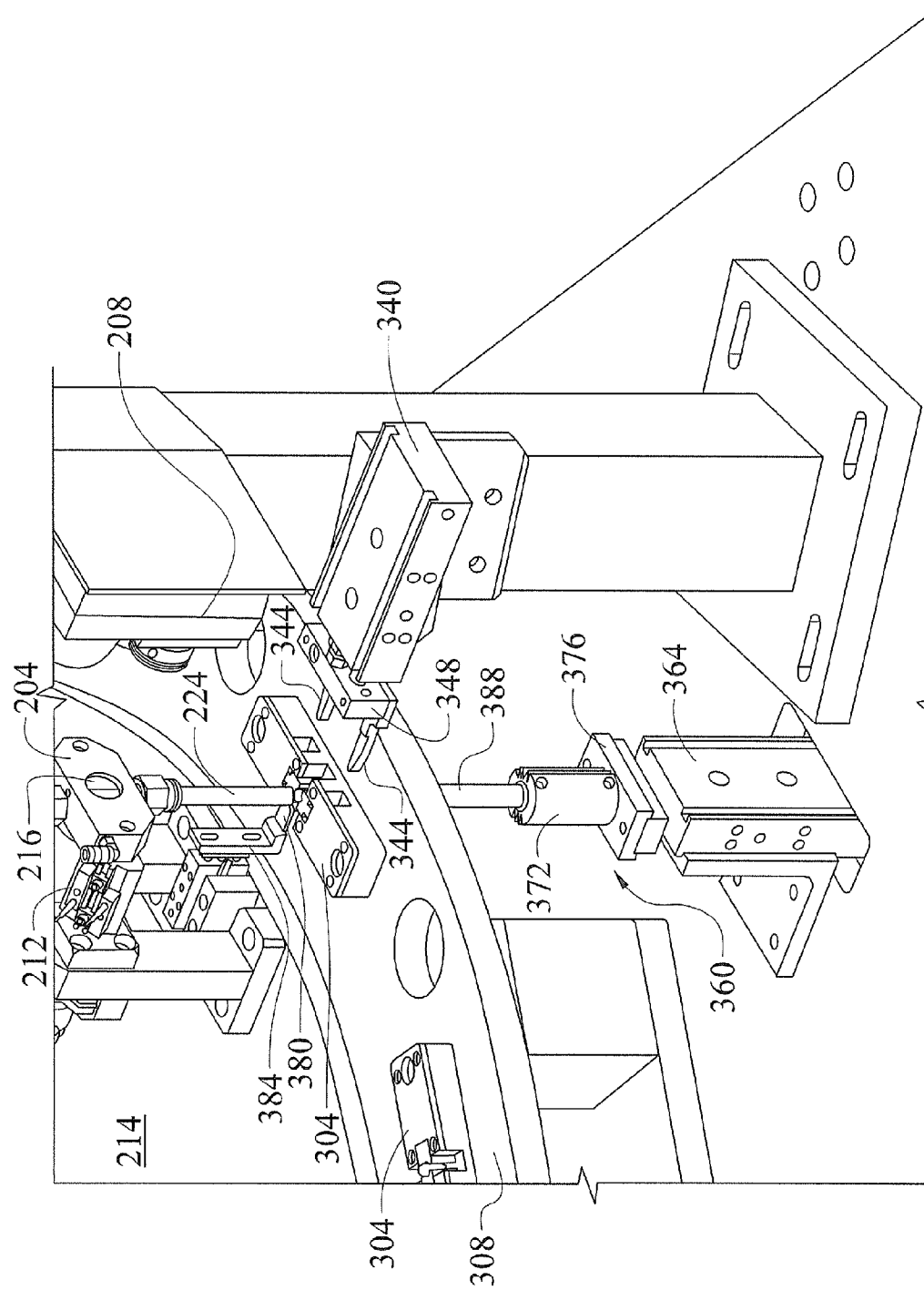
FIG. 5 is a perspective view of the seed orientation system shown in FIG. 3 including a seed holder, in accordance with various embodiments of the present disclosure.
Figure 6:
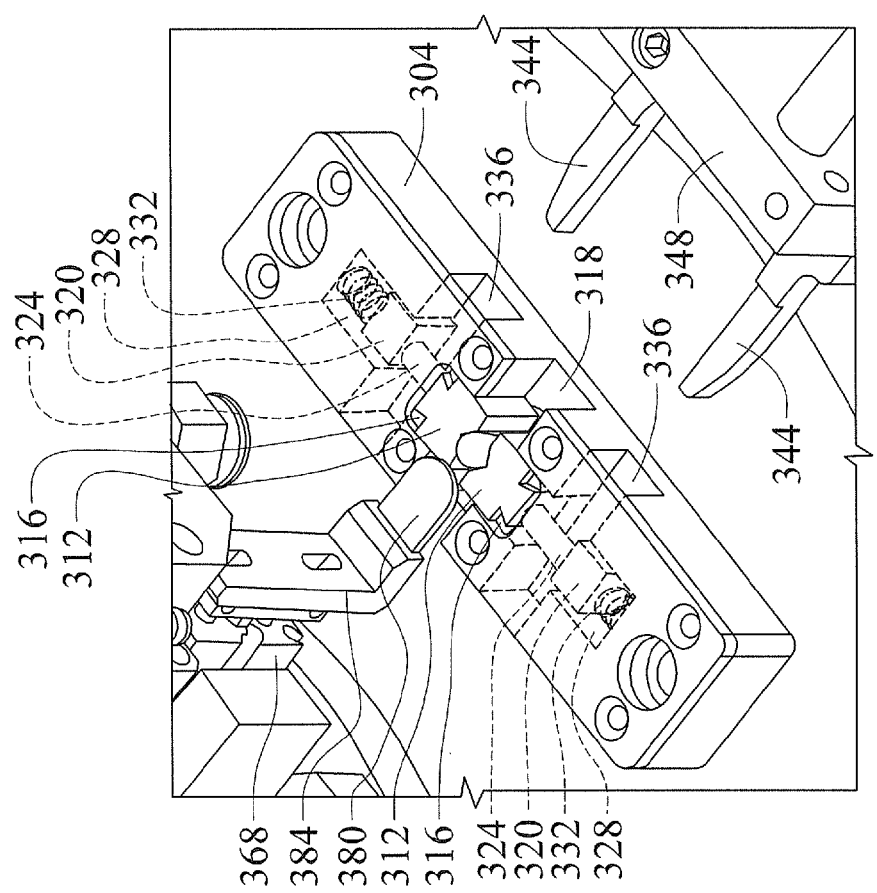
FIG. 6 is an enlarged perspective view of the seed holder shown in FIG. 5, in accordance with various embodiments of the present disclosure.
Figure 7:
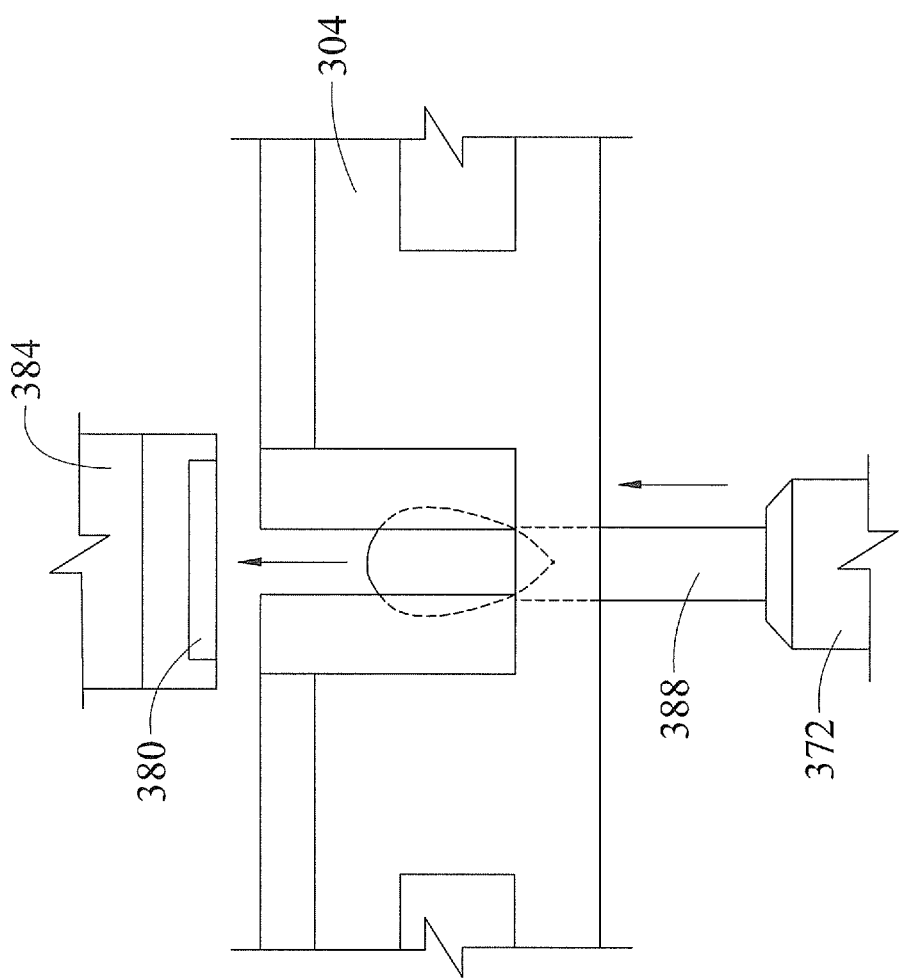
FIG. 7 is an enlarged side elevation view of the seed holder shown in FIG. 6, in accordance with various embodiments of the present disclosure.

Referring now to FIGS. 5, 6 and 7, each seed holder 304 is structured and used to rigidly retain a respective seed in the tip-down orientation. Each seed holder 304 includes a pair of opposing clamp heads 312 slidingly positioned within opposing clamp pockets 316. The opposing clamp pockets 316 are separated by a seed channel 318 laterally formed along a centerline C of the seed holder 304. Each clamp head 312 is connected to a respective clamp piston 320 via a respective clamp shaft 324. Each clamp piston 320 is slidingly housed within a respective longitudinal internal piston cylinder 328 of seed holder 304. A compression spring 332 is positioned within each piston cylinder 328 between a base of the respective piston and a bottom of the respective piston cylinder 328. Accordingly, each clamp head 312 is biased toward the centerline C of the seed holder 304. When a seed holder 304 is in an idle state, that is, when the respective seed holder is not holding a seed or being manipulated to hold a seed, the opposing clamp heads 312 will be biased by the springs 332 to a fully extended, or deployed, position. When the clamp heads 312 are in the deployed position, a top of each respective piston 320 will extend into a respective fork passageway 336 extending laterally through the seed holder 304 on opposing sides of the seed channel 318.

Each clamp head 312 is fabricated from a slightly soft, resilient material, such as neoprene, such that a seed held between the opposing clamp heads 312, as described below, will not be damaged.

As described above, the seed holders 304 are mounted to, and equally spaced around a perimeter area of, the turntable 308. Prior to, subsequent to, or substantially simultaneously with the seed orientation process described above, the turntable 308 is rotated to place an empty, i.e., absent a seed, seed holder 308 under the orientation system transfer tube 224. More specifically, the seed channel 318 is positioned under the orientation system transfer tube 224. When a seed holder 304 is positioned under the orientation system transfer tube 224 an automated clamp head spreader 340 is activated to spread the clamp heads 312 such that a seed can be received between the clamp heads 312. The clamp head spreader 340 is mounted to system support structure adjacent the seed orienting device 212 and includes a pair of fork tangs 344 coupled to a fork base 348. The clamp head spreader 340 is operable to extend the fork base 348 and tangs 344 toward the seed holder 304. For example, the clamp head spreader 340 can be a pneumatic device operable to extend and retract the fork base 348. Each fork tang 344 has a chamfered distal end portion and is sized to fit within the fork passageways 336.

Upon activation of the clamp head spreader 340, the fork base 348 is extended toward the seed holder 304 such that the tangs 344 are inserted into the fork passageways 336. As each tang 344 slides into the respective fork passageway 336 the chamfered distal end portions slide between the top of each respective piston 320 and an inner wall of the fork passageway 336. As the tangs 344 are extended further into each fork passageway 336, the chamfer of each tang forces the respective piston 320 outward and away from the centerline C of the seed holder. Accordingly, as the pistons 320 are moved outward and away from the centerline C, the clamp heads 312 are also moved outward and away from each other and the centerline C. Thus, the clamp heads 312 are moved to a retracted position where a seed can be placed between them.

Once the clamp heads 312 have been retracted, a properly oriented seed can be conveyed through the orientation system transfer tube 224 and positioned in the tip-down orientation between the clamp heads 312. In various embodiments, the seed sampler system 10 additionally includes a seed height positioning subsystem 360 for positioning the seed at a specific height within the respective seed holder 304. The seed height positioning subsystem includes a vertical positioner 364 mounted to system support structure below the perimeter area of the turntable 308, directly opposite the orientation system transfer tube 224, and a datum plate actuator 368 mounted to the center platform 214 directly opposite the clamp head spreader 340. The vertical positioner 364 includes a spring loaded plunger 372 mounted to a positioner head 376 and the datum plate actuator 368 includes a datum plate 380 mounted to a datum plate actuator head 384. The vertical positioner 364 is operable to extend the positioner head 376 and plunger 372 toward a bottom of the turntable 308 directly opposite the seed holder centerline C. For example, the vertical positioner 364 can be a pneumatic device operable to extend and retract the plunger 372. Similarly, the datum plate actuator 368 is operable to extend the actuator head 384 and datum plate 380 over the top of the seed holder seed channel 318. For example, the datum plate actuator 368 can be a pneumatic device operable to extend and retract the datum plate 380.

Once the seed has been positioned between the retracted clamp heads 312, the positioner head 376 is extended upward to insert a plunger shaft 388 through a hole (not shown) in the bottom of the turntable 308 and a coaxially aligned hole (not shown) in the bottom of the seed holder seed channel 318. Substantially simultaneously, the datum plate actuator 368 extends the actuator head 384 to position the datum plate 380 a specified distance above the seed holder 304, directly above the hole in the bottom of the seed holder seed channel 318. More specifically, as positioner head 376 is moved upward, the plunger shaft 388 is extended into the coaxially aligned holes and contacts the tip of the seed. The seed is then pushed upward between the clamp heads 312 until the crown of the seed contacts the datum plate 380. The spring loaded structure of the plunger 372 allows the shaft 388 to retract within the plunger 372 when the seed crown contacts the datum plate 380 so that the seed is held in place without damaging the seed. Accordingly, the crown of the seed is located at a specific height relative to the top of the turntable 308.

With the seed crown held against the datum plate 380 by the spring loaded plunger 372, the clamp head spreader 340 is operated to retract the fork base 348 and withdraw the tangs 344 from the respective passageways 336. Upon withdrawal of the tangs 344, the springs 332 bias the clamp heads 312 toward the deployed position and firmly clamp the seed between the clamp heads 312. The datum plate 380 and plunger shaft 388 are subsequently retracted leaving the seed properly positioned, or 'loaded', in the respective seed holder 304. The system controller then rotates the turntable 308 to position the 'loaded' seed holder 304 beneath the milling station 400 and the next empty seed holder 304 beneath the seed orienting device 212.

Figure 8:
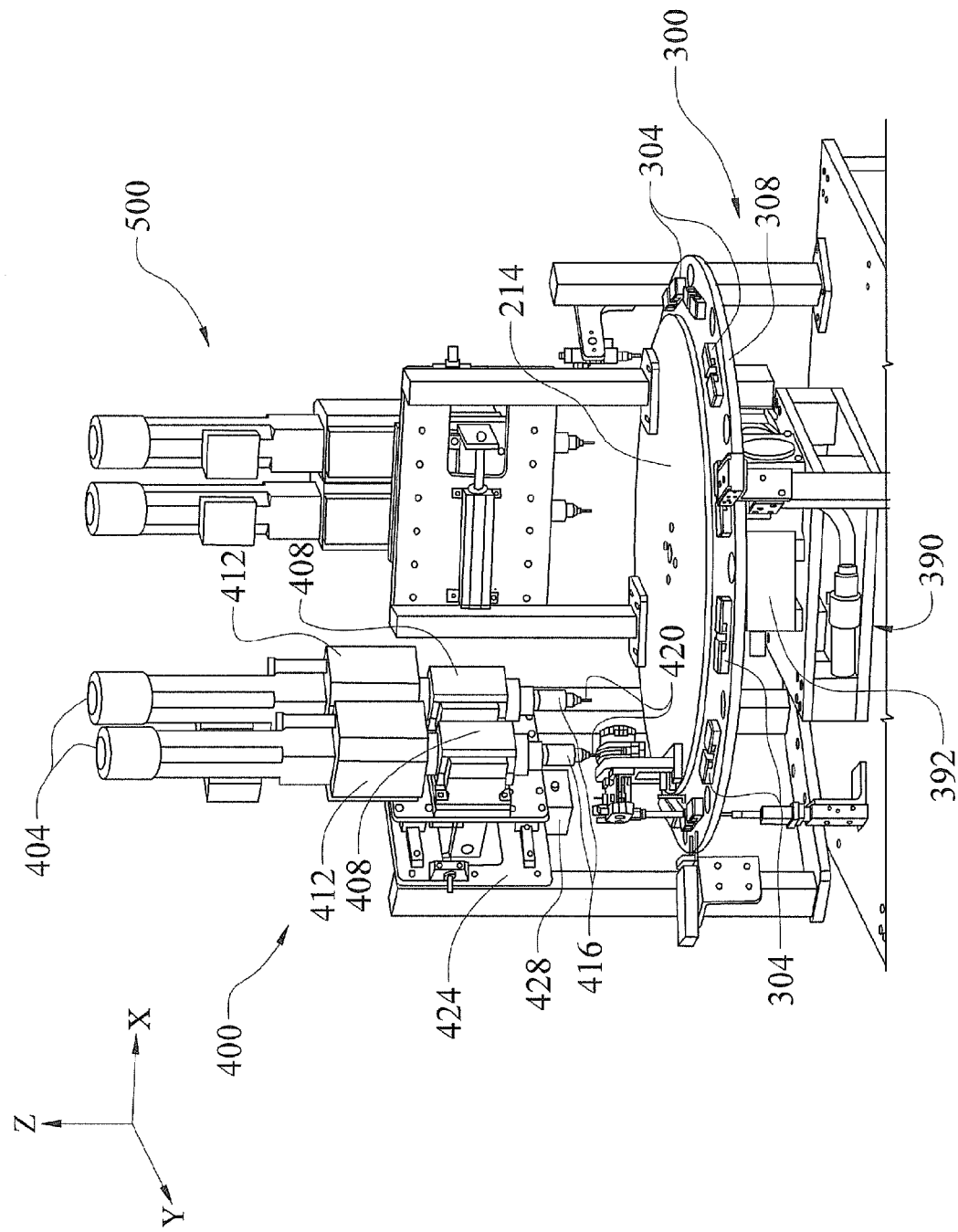
FIG. 8 is a perspective view of a milling station and a seed transport subsystem of the seed sampler system shown in FIG. 1, in accordance with various embodiments of the present disclosure.

Referring now to FIG. 8, as described above, the seed sampler system 10 includes the seed transport subsystem 300 for conveying the seeds between individual stations of the sampler system, e.g., the seed loading station 100, milling station 400, sampling station 500, etc. Generally, the seed transport subsystem 300 can be any suitable conveyance mechanism such as, for example, a belt conveyor, roller conveyor, and the like. In various embodiments, however, the transport subsystem 300 comprises the round turntable 308 that is pivotally mounted at its center for rotation. The turntable 308 is virtually divided into a plurality of sectors, with each sector containing a seed holder 304. The number of sectors available on the turntable 308 may be even or odd with a number chosen which depends in large part on the diameter of the turntable 308, the size of the seed holders 304 and the needs of the transport application.

The circular turntable 308 is pivotally mounted at its center to a shaft and bearing system 390. In various embodiments, a shaft (not shown) of the shaft and bearing system 390 can be directly coupled to an actuating motor 392. Alternatively, the shaft may be separate from the actuating motor 392 and driven for rotation by a suitable chain drive, pulley drive or gear drive. In various implementations, the actuating motor 392 can be a high torque stepper motor.

In operation, the actuating motor 392 for the turntable 308 is actuated to step forward (which can be either clockwise or counter clockwise, depending on configuration) to rotationally move the turntable 308 from station to station of the sampler system 10. Therefore, the seed holders 304 are aligned with auxiliary devices, such as the loading station 100, milling station 400, sampling station 500, etc. In this configuration, an auxiliary device can be positioned about the turntable 308 at stations which are in alignment with each position and thus have precise access to the seeds and seed holders 304. To the extent necessary, the peripheral edges of the turntable 308 may be supported with rollers, guides, slides, or the like, to assist with smooth rotation of the turntable conveyor.

Referring to FIG. 8 further, as described above, once each seed holder 304 is 'loaded' with a seed, the system controller rotates the turntable 308 to position the 'loaded' seed holder 304 beneath the milling station 400. The milling station 400 includes at least one milling tool 404 mounted to system support structure above the perimeter area of the turntable 308. The one or more milling tools 404 are used to remove a portion of the seed coat from each seed when the respective seed holder 304 is positioned beneath the milling station 400. Each milling tool 404 includes a Z-axis actuator 408 operable to lower and raise at least a portion of the respective milling tool 404 along the Z-axis. Each milling tool 404 is controlled by the system controller and can be electrically, pneumatically or hydraulically operated.

The milling tool(s) 404 can be any suitable mechanism for removing a portion of seed coat material from each seed. For example, in various embodiments, each milling tool 404 is a rotary device including the Z-axis actuator 408 and a rotary drive 412 operationally coupled to a bit chuck 416. Each Z-axis actuator 408 is operable to lower and raise the respective bit chuck 416 and a milling tool bit 420 held within the bit chuck 416 along the Z-axis. The milling tool bit 420 can be any instrument suitable for removing the seed coat material, such as a mill bit, drill bit, a router bit, a broach, or a scraping tool. For example, in various embodiments, the milling tool bit 420 comprises an end mill bit. Each Z-axis actuator 408 is controlled by the system controller to lower the respective Z-axis actuator 408 a specific predetermined distance. The rotary drive 412 of each rotary milling tool 404 functions to rotate, or spin, the respective bit chuck 416 and any milling tool bit 420 held within the bit chuck 416.

In operation, when a seed holder 304 is positioned below a rotary milling tool 404, the rotary drive 412 is activated to begin spinning the bit chuck 416 and milling tool bit 420. The Z-axis actuator 408 is then commanded to lower the respective bit chuck 416 and milling tool bit 420 a specific predetermined distance. As the spinning milling tool bit 420 is lowered, it contacts the crown of the seed and removes the seed coat from at least a portion of the crown. This exposes a portion of the inner seed material that can be extracted and utilized to test and analyze the various traits of the respective seed, as described below.

In various embodiments, the milling station 400 comprises at least two milling tools 404 mounted to a milling station horizontal movement stage 424 that is mounted to system support structure. The milling station horizontal movement stage 424 is controlled by the system controller to position a selected one of the milling tools 404 above a seed holder 304 positioned below the milling station 400. The selected milling tool 404 is then operated as described above to remove the seed coat from at least a portion of the respective seed crown.

Subsequently, the system controller can position a second one of the milling tools 404 above a subsequent seed holder 304 positioned below the milling station 400. The second selected milling tool 404 is then operated as described above to remove the seed coat from at least a portion of the respective seed crown. In such embodiments, the milling station 400 can additionally include at least one milling bit cleaning assembly 428 for cleaning the bit 416 of the idle, i.e., not in use, milling tool 404. That is, while one milling tool 404 is operable to remove the seed coat from a respective seed, the bit 420 of an idle second milling tool 404 can be cleaned by a cleaning assembly 428 in preparation for the next milling operation. In various embodiments, the milling bit cleaning assemblies 428 utilize air pressure and or vacuum pressure to remove and/or collect any seed coat residue that may collect on the bits 420 of the milling tools 404.

Figure 9:
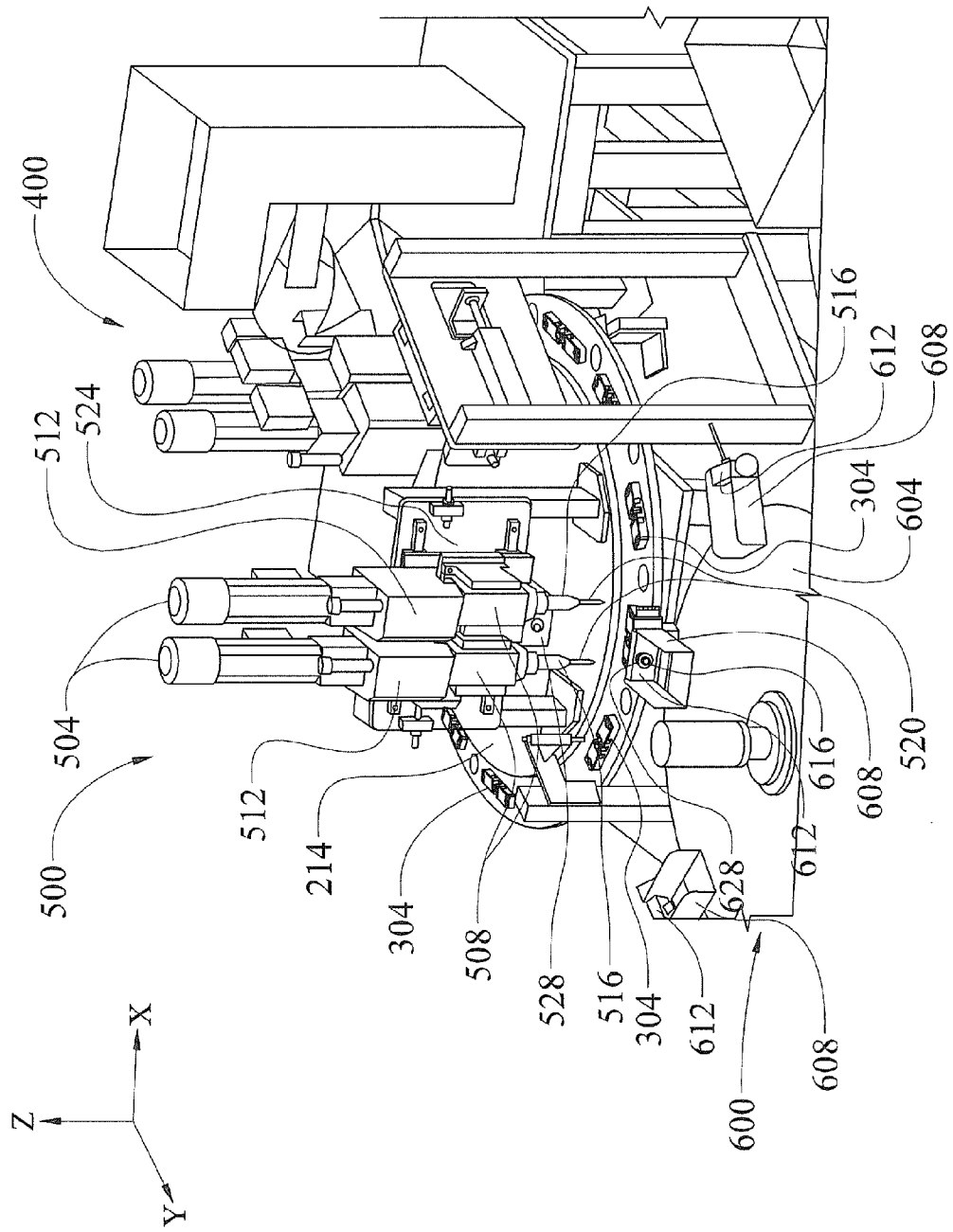
FIG. 9 is a perspective view of a sampling station of the seed sampler system shown in FIG. 1, in accordance with various embodiments of the present disclosure.

Referring now to FIG. 9, once the seed coat has been removed from a seed, the system controller rotates the turntable 308 to position the respective seed holder 304 beneath the sampling station 500. The sampling station 500 includes at least one sampling tool 504 mounted to system support structure anchored to the center platform 214 above the turntable 308. The one or more sampling tools 504 are used to remove a portion, i.e., a sample, of the exposed inner seed material when the respective seed holder 304 is positioned beneath the sampling station 500. Each sampling tool 504 includes a Z-axis actuator 508 operable to lower and raise at least a portion of the respective sampling tool 504 along the Z-axis. Each sampling tool 504 is controlled by the system controller and can be electrically, pneumatically or hydraulically operated.

The sampling tool(s) 504 can be any suitable mechanism for removing a sample of the exposed inner seed material from each seed. For example, in various embodiments, each sampling tool 504 is a rotary device including the Z-axis actuator 508 and a rotary drive 512 operationally coupled to a bit chuck 516. Each Z-axis actuator 508 is operable to lower and raise the respective bit chuck 516 and a sampling tool bit 520 held within the bit chuck 516 along the Z-axis. The sampling tool bit 520 can be any instrument having an outer diameter smaller than the circumference of the area of exposed inner seed material, and suitable for removing a sample from the exposed inner seed material, such as a drill bit, a router bit, a broach, or a coring tube. It is important that the sampling tool bit 520 be of a smaller diameter than the milling tool bit 420 to ensure that sample material is obtained from an area where the seed coat material has been removed, thereby substantially eliminating any seed coat material from contaminating the sample material collected.

For example, in various embodiments, the sampling tool bit 520 comprises a spade tip drill bit having an outer diameter that is smaller than an outer diameter of the milling tool bit 420. Each Z-axis actuator 508 is controlled by the system controller to lower the respective Z-axis actuator 508 a specific predetermined distance. The rotary drive 512 of each rotary sampling tool 454 functions to rotate, or spin, the respective bit chuck 516 and any sampling tool bit 520 held within the bit chuck 516.

In operation, when a seed holder 304 is positioned below a rotary sampling tool 504, the rotary drive 512 is activated to begin spinning the bit chuck 516 and sampling tool bit 520. The Z-axis actuator 508 is then commanded to lower the respective bit chuck 516 and sampling tool bit 520 a specific predetermined distance. As the spinning sampling tool bit 520 is lowered, it contacts the exposed inner material of the seed and cuts away a sample of the inner material. The sample is then removed, or extracted, to be tested and analyzed for various traits and/or characteristics of the respective seed, as described below.

In various embodiments, the sampling station 500 comprises at least two sampling tools 504 mounted to a sampling station horizontal movement stage 524 that is mounted to system support structure. The sampling station horizontal movement stage 524 is controlled by the system controller to position a selected one of the sampling tools 504 above a seed holder 304 positioned below the sampling station 500. The selected sampling tool 504 is then operated as described above to remove the sample from the exposed inner material of the respective seed. Subsequently, the system controller can position a second one of the sampling tools 504 above a subsequent seed holder 304 positioned below the sampling station 500. The second selected sampling tool 504 is then operated as described above to remove the sample from the exposed inner material of the respective seed. In such embodiments, the sampling station 500 can additionally include at least one sampling bit cleaning assembly 528 for cleaning the sampling bit 520 of the idle, i.e., not in use, sampling tool 504. That is, while one sampling tool 504 is operable to remove the sample from a respective seed, the sampling bit 520 of an idle second sampling tool 504 can be cleaned by a sampling bit cleaning assembly 528 in preparation for the next sampling operation. In various embodiments, the sampling bit cleaning assemblies 528 utilize air pressure and or vacuum pressure to remove and/or collect any inner seed material residue that may collect on the sampling bits 520 of the sampling tools 504.

Figure 10:
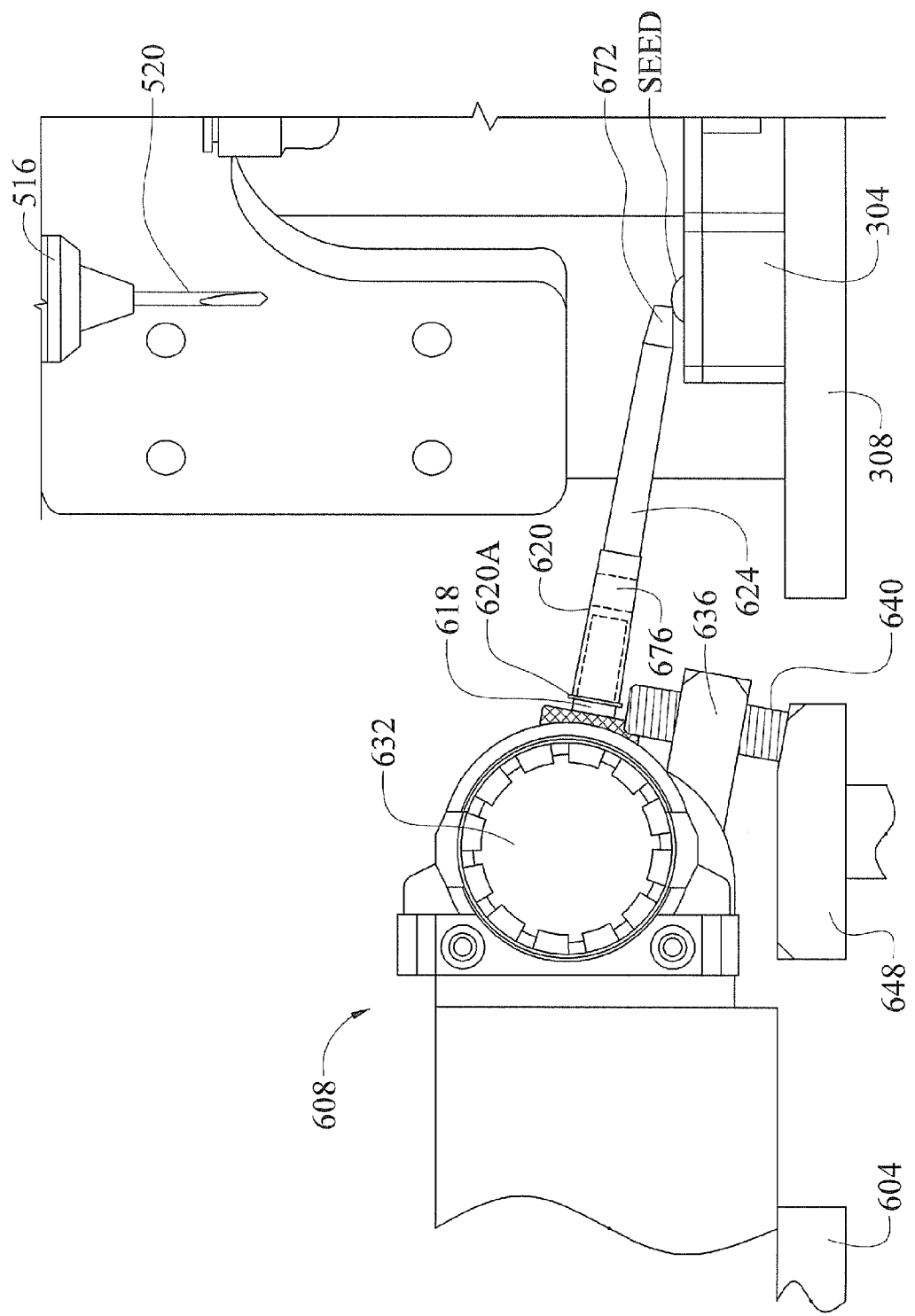
FIG. 10 is an enlarged side elevation view of the seed sampling station, shown in FIG. 9, during operation of the seed sampler system shown in FIG. 1, in accordance with various embodiments of the present disclosure.

Referring now to FIGS. 9 and 10, the sample collection and transport (SCT) subsystem 600 is controlled by the system controller to operate in synchronized coordination with the sampling station 500 to collect each sample as it is removed from each seed. The SCT subsystem 600 includes a motorized rotating platform 604 driven by an actuating motor (not shown) similar to the turntable 308 actuating motor 392 (shown in FIG. 8). The SCT subsystem additionally includes a plurality of collection tube placement (CTP) devices 608 equally spaced around, and mounted to a perimeter area of the rotating platform 604. Each CTP device 608 includes a pivot bar 612 having a hollow tube mount 616 mounted through a transverse bore (not shown) in the pivot bar 612. The tube mount 616 includes a distal end 618 structured to accept a base 620 of a collection tube 624 and a proximal end 628 adapted to receive pneumatic tubing (not shown).

Figure 11:
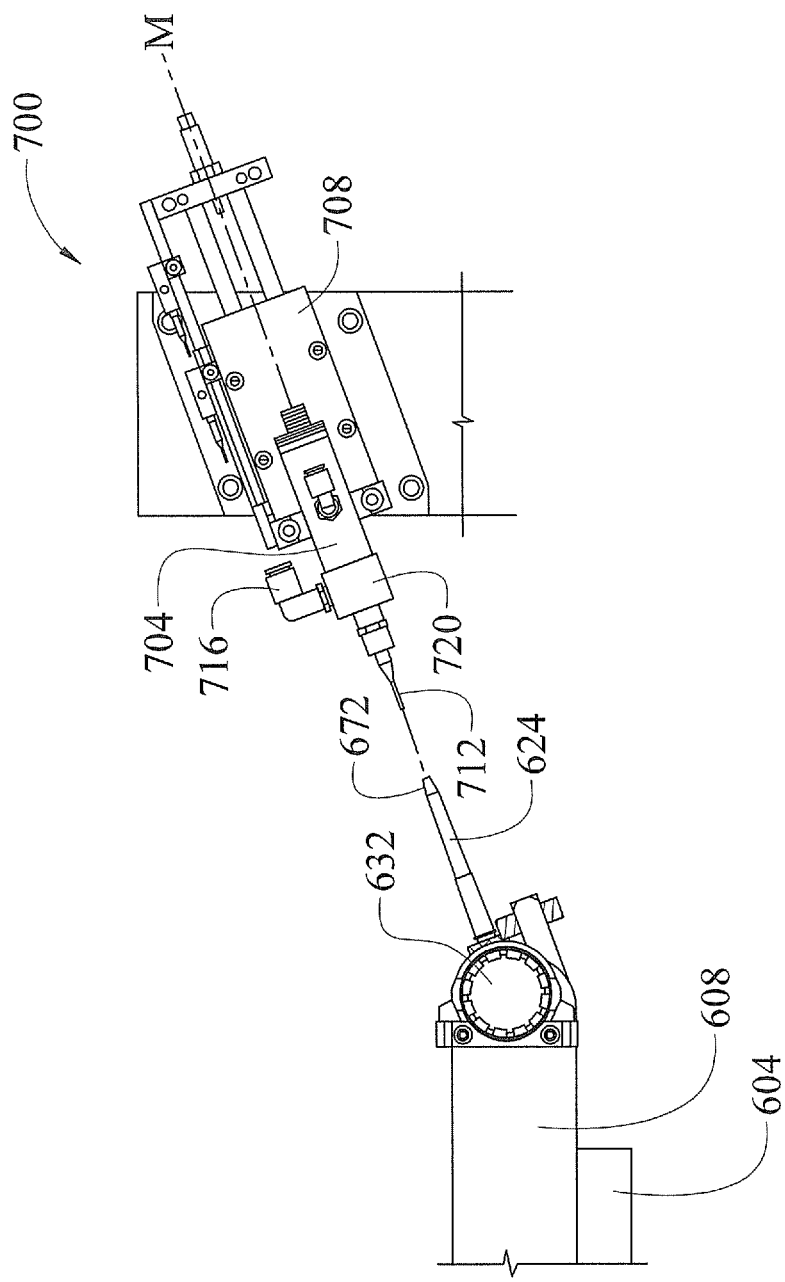
FIG. 11 is a side elevation view of a liquid delivery apparatus of the seed sampling system, shown in FIG. 1, in a retracted position, in accordance with various embodiments of the present disclosure.
Figure 13:
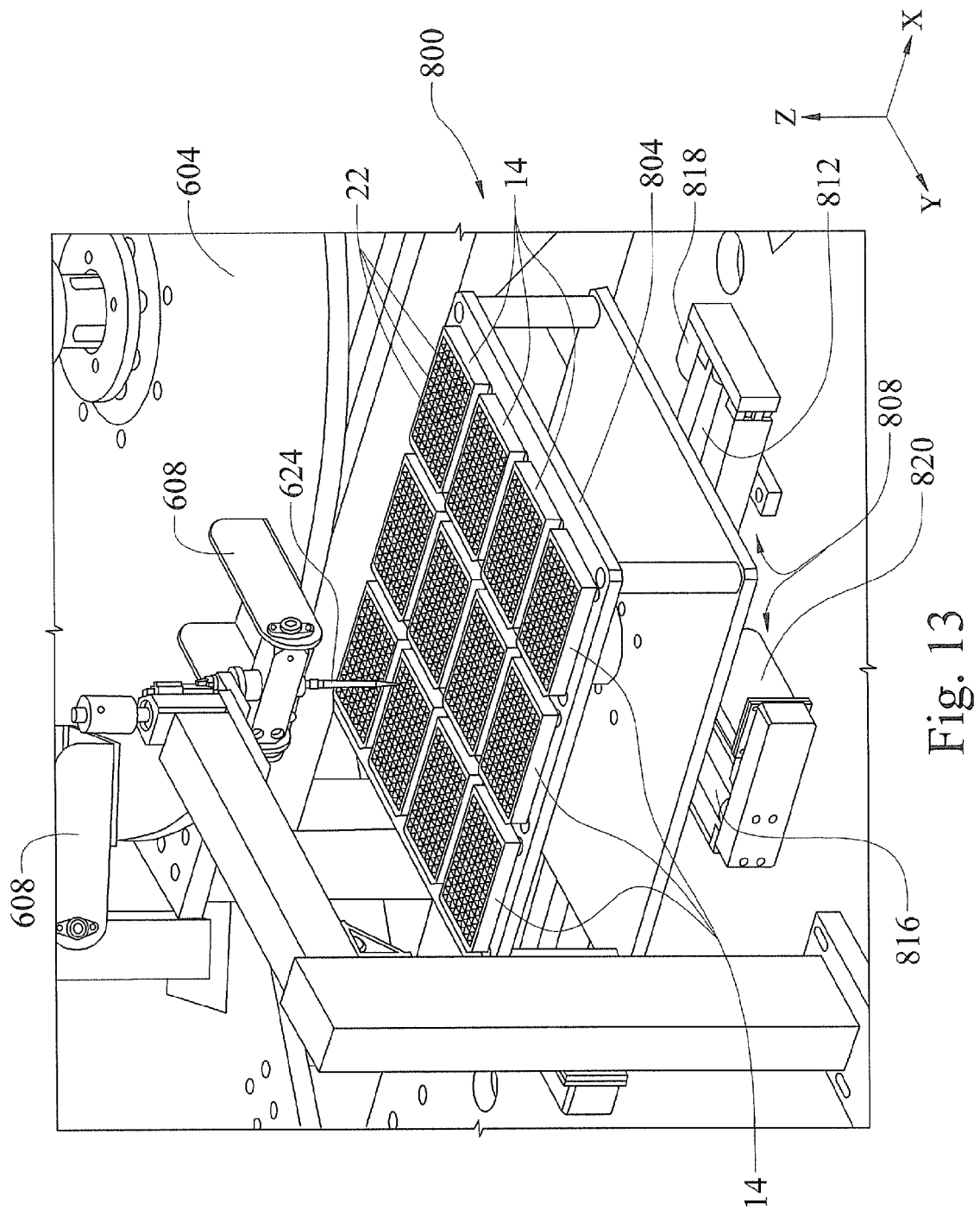
FIG. 13 is a perspective view of a sample tray platform of the seed sampler system shown in FIG. 1, in accordance with various embodiments of the present disclosure.
Figure 17:
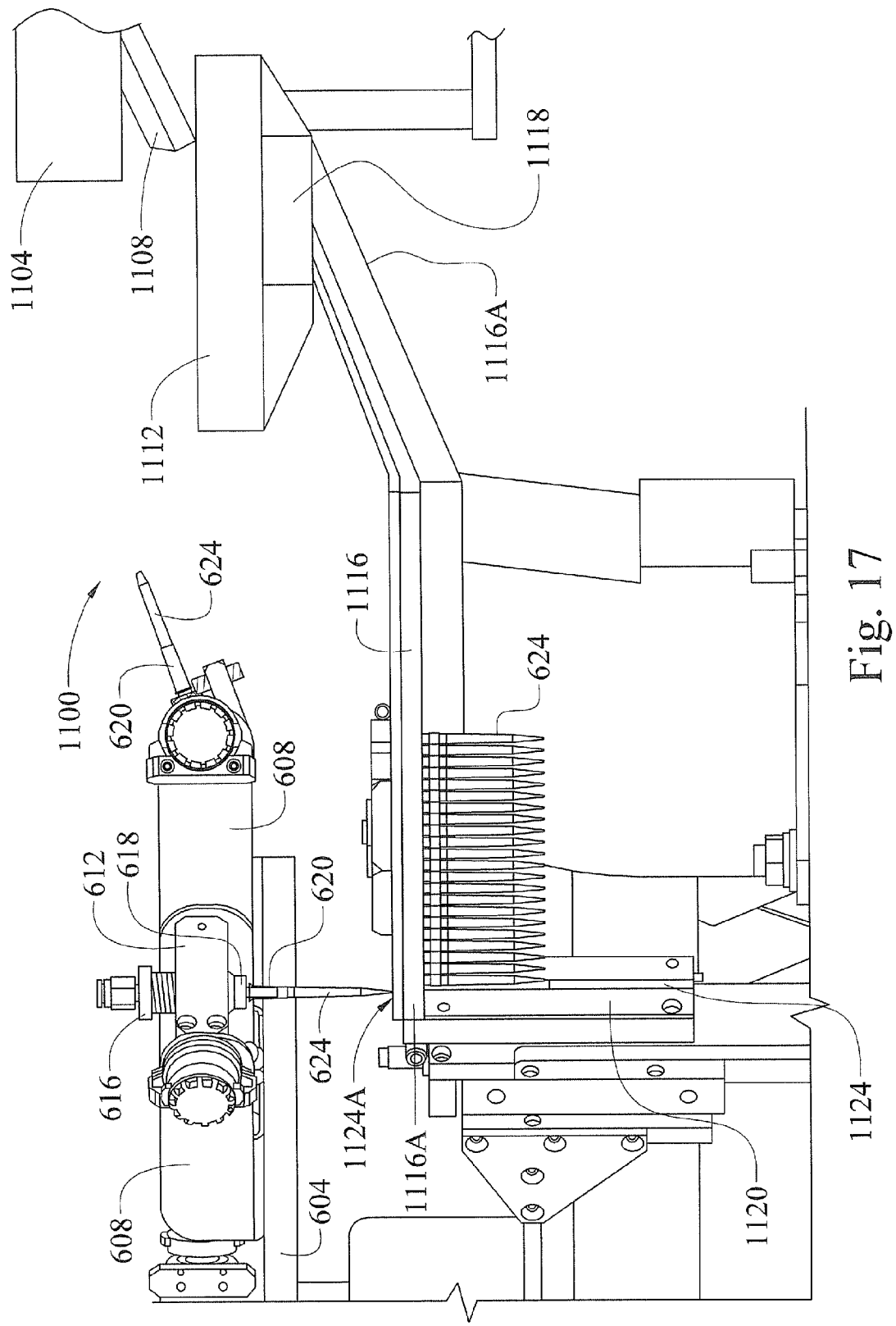
FIG. 17 is a side elevation view of a collection tube loading station of the seed sampler system shown in FIG. 1, in accordance with various embodiments of the present disclosure.

Each CTP device 608 further includes a pivot bar actuator 632 controllable by the system controller to rotate the pivot bar 612 to various positions about a longitudinal axis of the pivot bar 612. In various embodiments, the pivot bar actuator 632 is operable to pivot the tube mount 616 between a flushing position, as illustrated in FIG. 11, a collection position, as illustrated in FIG. 10, and a load and deposit position, as illustrated in FIGS. 13 and 17. The CTP device 608 additionally includes a stop arm 636 connected to the pivot bar 612 and an adjustable stop 640, e.g., a set screw, adjustably engaged with the stop arm 636. The stop arm 636 and adjustable stop 640 pivot with the pivot bar 612 and function to accurately stop rotation of the pivot bar 612 so that the tube mount 616 is in the collection position.

Simultaneously with the operation of the seed loading station 100, the milling station 400 and the sampling station 500, the SCT subsystem 600 operates to load the collection tube 624 on the tube mounts 616 of each CTP device 608, collect the samples in the collection tubes 624 as each sample is being removed, and deposit the collected samples in the sample trays 14. Loading the collection tubes 624 on the tube mounts 616 and depositing the collected sample in the sample trays 14, will be described further below with reference to FIG. 17, and FIGS. 12 and 13, respectively. The collection tubes 624 can be any container or device suitable for mounting on the tube mounts 616 and collecting the samples as described below. For example, in various embodiments, the collection tubes 624 are disposable such that each sample is collected in a clean collection tube 624. An example of such a disposable collection tube 624 is a filtered pipette.

As described above, the SCT subsystem 600 is controlled by the system controller to operate in synchronized coordination with the sampling station 500 to collect each sample as it is removed from each seed. More specifically, prior to removing the sample from the seed, the system controller rotates the platform 604 to position a CTP device 608 adjacent the sampling station 500. Particularly, a CTP device 608 is positioned adjacent the sampling station 500 such that the respective tube mount 616 is aligned with the seed held within an adjacent seed holder 304 that has been positioned below a sampling device 504, via the controlled rotation of the turntable 308. Prior to positioning the CTP device 608 adjacent the seed holder 304 positioned at the sampling station 500, the SCT system 600 has loaded a collection tube 624 on the respective tube mount distal end 618 and the respective pivot bar actuator 632 has raised the collection tube 624 to a position above the collection position, e.g., the flushing position. Once the CTP device 608 is positioned adjacent the respective seed holder 304, the pivot bar actuator 632 lowers the loaded collection tube 624 until the adjustable stop 640 contacts a stop plate 648 mounted to system support structure between the turntable 308 and the platform 604 adjacent the sampling station 500. The adjustable stop 640 is preset, i.e., pre-adjusted, such that the rotation of the pivot bar 612 is stopped to precisely locate a tip 672 of the collection tube 624 in very close proximity to, or in contact with, the crown of the seed held in the adjacent seed holder 304.

The sampling bit 620 of a sampling tool 504 is then lowered to begin removing the sample, as described above. As sampling bit 620 is lowered, a vacuum is provided at the collection tube tip 672. The vacuum is provided via vacuum tube (not shown) connected to the proximal end 628 of the tube mount 616. The vacuum tube is also connected to a vacuum source (not shown) such that the vacuum is through the vacuum tube, the hollow tube mount 616 and the collection tube 624. Accordingly, as the sampling bit 620 removes the sample material, the sample is drawn into the collection tube 624, where the sample is collected. In various embodiments, the sampling station 500 can include a positive pressure device (not shown) to assist the vacuum provided at the respective seed to collect substantially all the removed sample in the respective collection tube 624.

Each collection tube includes a filter 676 that prevents the sample from being drawn into the tube mount 616 and vacuum tube. Once the sample has been collected, the pivot bar actuator 632 raises the collection tube 624 to the flush position and the respective CTP device 608 is advanced to a position adjacent the liquid delivery subsystem 700. Consequently, another CTP device 608 and empty collection tube 624 are positioned adjacent a subsequent seed holder 304 and un-sampled seed that have been moved to the sampling station.

Figure 12:
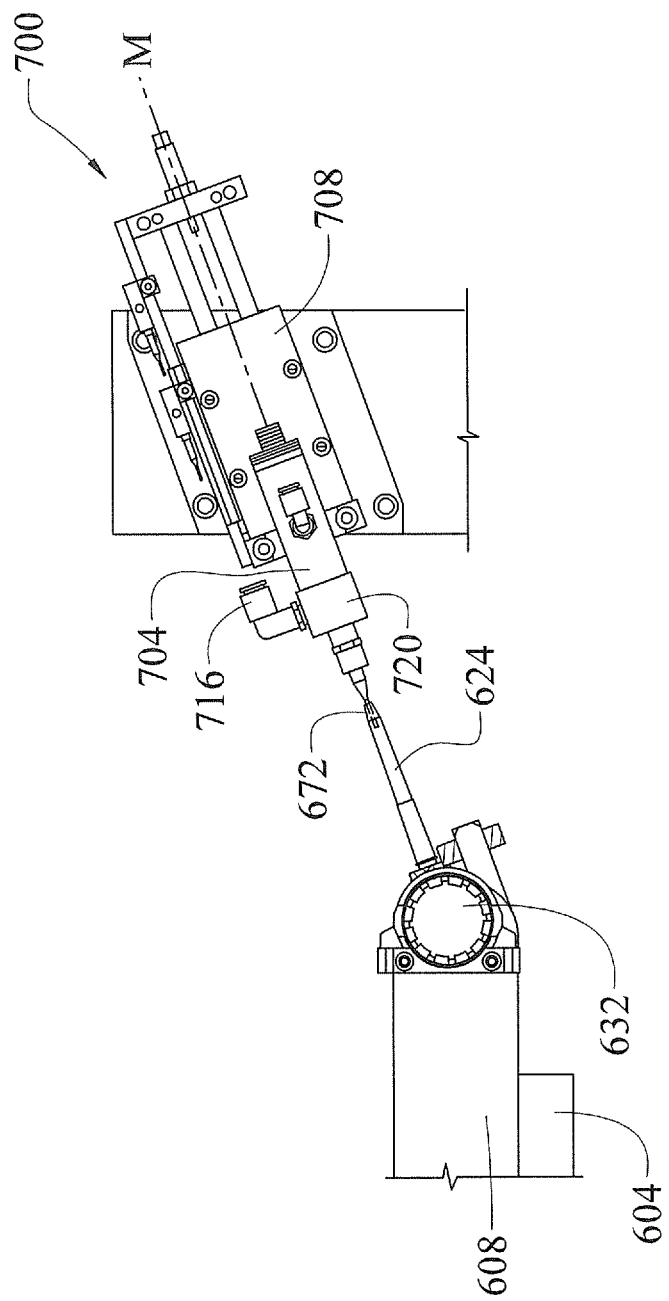
FIG. 12 is a side elevation view of the liquid delivery apparatus shown in FIG. 11, in an extended position, in accordance with various embodiments of the present disclosure.

Referring now to FIGS. 11 and 12, the liquid delivery subsystem 700 includes a liquid injection device 704 mounted to a linear actuator 708 operable to extend and retract the liquid injection device 704 along a linear axis M. More specifically, the linear actuator 708 is operable to insert and withdraw an injection needle 712, fastened to the liquid injection device 704, into and out of the tip 672 of the respective collection tube 624. When a collection tube 624 with a collected sample has been raised to the flush position and advanced to be positioned adjacent the liquid delivery subsystem 700, the linear actuator 708 and injection needle 712 are in the retracted position, as illustrated in FIG. 11. The pivot bar actuator 632 and rotating platform 604 are controlled by the system controller such that when the CTP device 608 is adjacent the liquid delivery subsystem 700 and the collection tube 624 is raised to the flush position, a linear axis of the collection tube 624 is substantially coaxial with the linear axis M of the liquid injection device 704, as shown in FIG. 11.

Once the linear axis of the collection tube 624 is positioned to be coaxial with the M axis, the linear actuator 708 extends to insert the injection needle 712 into the tip 672 of the collection tube 624. The liquid injection device 704 is connected to an extraction fluid supply source (not shown) via a fluid port 716 coupled to a metering valve 720 of the liquid injection device 704. Therefore, once the injection needle 712 is inserted into the collection tube tip 672, the fluid injection device 704 injects a metered amount of extraction fluid into the collection tube 624. The injected extraction fluid flushes, or washes, the interior sides of the collection tube 624 and creates an aqueous solution with the respective sample, herein referred to as an aqueous sample. Thus, any of the collected sample that may have gathered on the interior walls of the collection tube 624 is flushed off so that substantially all the collected sample is suspended in the resulting aqueous solution. The extraction liquid can be any liquid suitable for delivering substantially all the sample material collected within each respective collection tube 624, without interfering with the desired analysis, e.g., chemical and genetic analysis, of the sample material. For example, in various embodiments, the extraction liquid may comprise distilled water or any suitable solvent compatible with the desired sample analysis.

Once the collected sample has been mixed with the extraction liquid, the linear actuator 708 retracts to withdraw the injection needle 712 from collection tube tip 672. The system controller then advances the rotating platform 604 to position the CTP device 608 above the sample deposit subsystem 800. The system controller additionally commands the respective pivot bar actuator 632 to position the collection tube in the load and deposit position. The load and deposit position points the tube mount 616 and mounted collection tube 624 downward to a substantially vertical orientation.

Referring now to FIG. 13, the sample deposit subsystem 800 includes a sample tray platform 804 adapted to securely retain a plurality of sample trays 14 in fixed positions and orientations. Each sample tray 14 includes a plurality of sample wells 22, each of which are adapted for receiving a collected aqueous sample. The sample tray platform 804 is mounted to an X-Y stage 808. The X-Y stage 808 is a two-dimensional translation mechanism, including a first translating track 812 and a second translating track 816. The X-Y stage 808 additionally includes a first linear actuator 818 operable to bidirectionally move a first carriage (not shown) along the length of the first translating track 812. The X-Y stage 808 further includes a second linear actuator 820 operable to bidirectionally move a second carriage (not shown) along the length of the second translating track 816. The second translating track 816 is mounted to the first carriage and the sample tray platform 804 is mounted to the second carriage.

The first and second linear actuators 818 and 820 are controlled by the system controller to precisely move the sample tray platform 804 in two dimensions. More particularly, the first and second actuators 818 and 820 move the sample tray platform 804 within an X-Y coordinate system to precisely position any selected well 22 of any selected sample tray 14 at a target location beneath the CTP device 608 holding the collection tube 624 containing the collected aqueous sample. The target location is the location in the X-Y coordinate system that is directly below the collection tube tip 672 when the collection tube 624 is in the load and deposit position above the sample tray platform 804. Thus, once the CTP device 608 is positioned above the sample tray platform 804 and the respective collection tube 624 is placed in the load and deposit position, with the tip 672 pointing at the target location, the system controller positions a selected well 22, of a selected sample tray 14 at the target location. The aqueous sample is then deposited into the selected well 22 by providing positive pressure to the proximal end 628 of tube mount 616.

As the sample trays 14 are placed on the sample tray platform 804, a tray identification number, e.g., a bar code, for each sample tray 14 and the location of each sample tray 14 on the platform 804 is recorded. Additionally, as each aqueous solution is deposited in a well 22, an X-Y location of the well, i.e., the target location, on the sample tray platform 804 can be recorded. The recorded tray and well positions on the sample tray platform 804 can then be compared to the X-Y locations of each deposited aqueous sample, to identify the specific aqueous sample in each well 22 of each sample tray 14.

Once each aqueous sample is deposited into a selected well 22, the system controller advances the rotating platform 604 to position a subsequent CTP device 608, holding a collection tube 624 containing a subsequent aqueous sample, above the sample deposit subsystem 800. Additionally, the CTP device 608 holding the used, empty collection tube 624 is advanced to a collection tube discard station 850 (shown in FIG. 1) where the used collection tube 624 can be removed or ejected from the respective tube mount 616 and discarded. Referring briefly to FIG. 1, in various embodiments, the collection tube discard station 850 includes a collection tube removal device 854 mounted to a linear actuator 858 operable to extend and retract an automated gripper 862. When a CTP device 608 holding a used collection tube 624 is positioned adjacent the collection tube removal device 854, the system controller commands the linear actuator 858 to extend and gripper 862 to grasp the used collection tube 624. The system controller then commands the linear actuator 858 to retract, thereby removing the used collection tube 624 from the respective tube mount 616. The gripper 862 can then be commanded to release the used collection tube 624 allowing it to fall into a discard container (not shown).

Figure 14:
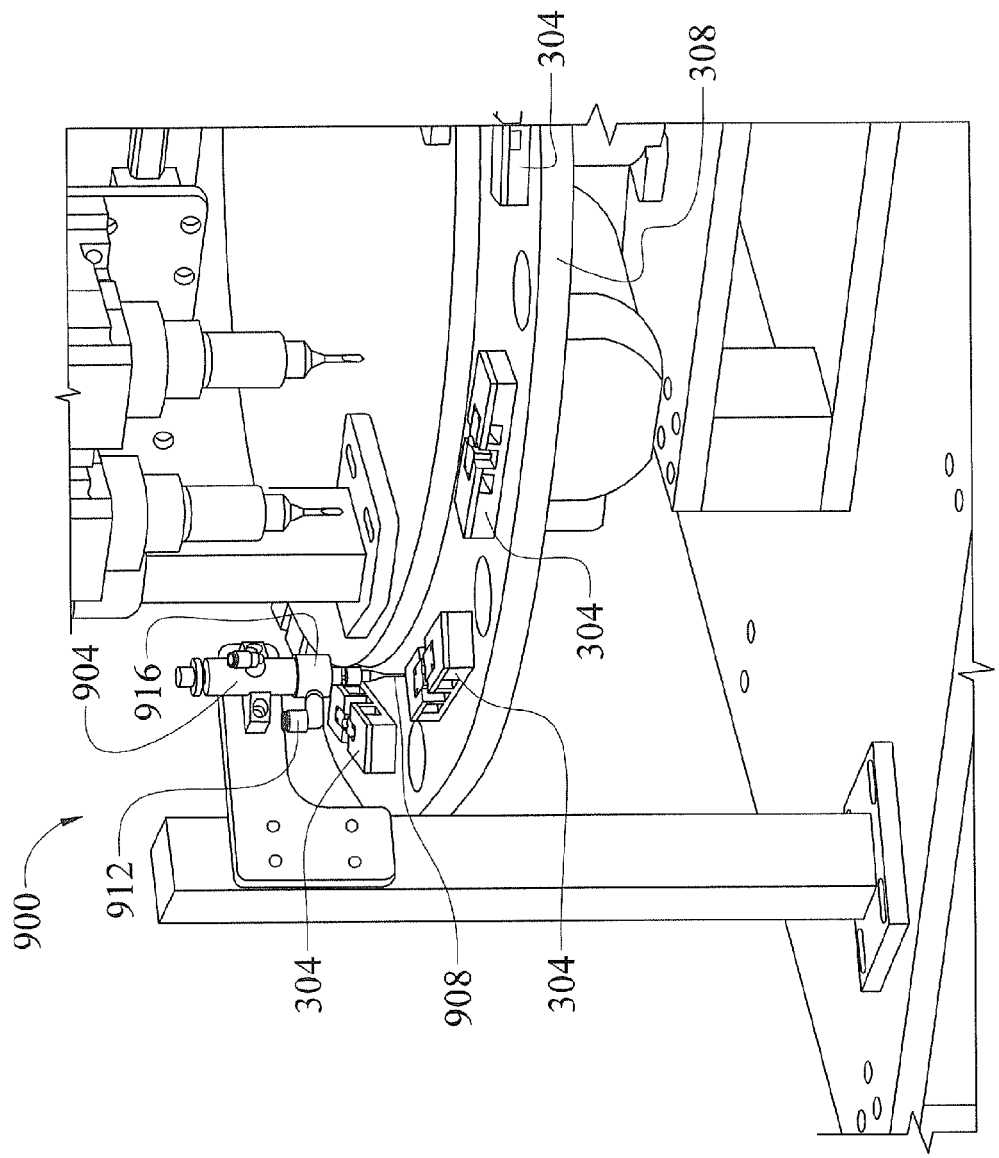
FIG. 14 is a perspective view of a seed treatment station of the seed sampler system shown in FIG. 1, in accordance with various embodiments of the present disclosure.

Referring now to FIG. 14, in various embodiments, after a seed has had a sample extracted at the sampling station 500, the system controller may advance the turntable 308 to position the respective seed holder 304 adjacent a seed treatment station 900. The seed treatment station 900 includes a treatment dispenser 904 mounted to system support structure above the perimeter area of the turntable 308. The treatment dispenser 904 includes an applicator 908 configured to apply a seed treatment such as a sealant to the exposed portion of the respective seed, i.e., the area of the seed crown where the seed coat has been removed and the sample extracted. The seed treatment can be any substance designed to enhance one or more properties of the seed or to protect the seed from bacteria or other harmful elements that could damage the seed and destroy the germination viability of the seed. For example, in various embodiments, the seed treatment is a sealant comprising a fungicide and/or polymer delivered to the seed by the treatment dispenser 904 via the applicator 908. The applicator 908 can be any device suitable to apply the desired seed treatment to the seeds, for example, a brush, needle or nozzle. In various embodiments, the applicator 908 comprises a spray nozzle and the treatment dispenser 904 includes a fluid port 912 coupled to a metering valve 916. In such embodiments, the treatment dispenser 904 is connected to liquid seed treatment supply source (not shown) via the fluid port 912. Accordingly, when a seed holder 304 is positioned at the seed treatment station 900, beneath the treatment dispenser 904, the system controller commands the treatment dispenser 904 spray a metered amount of seed treatment on the respective seed.

Figure 15:
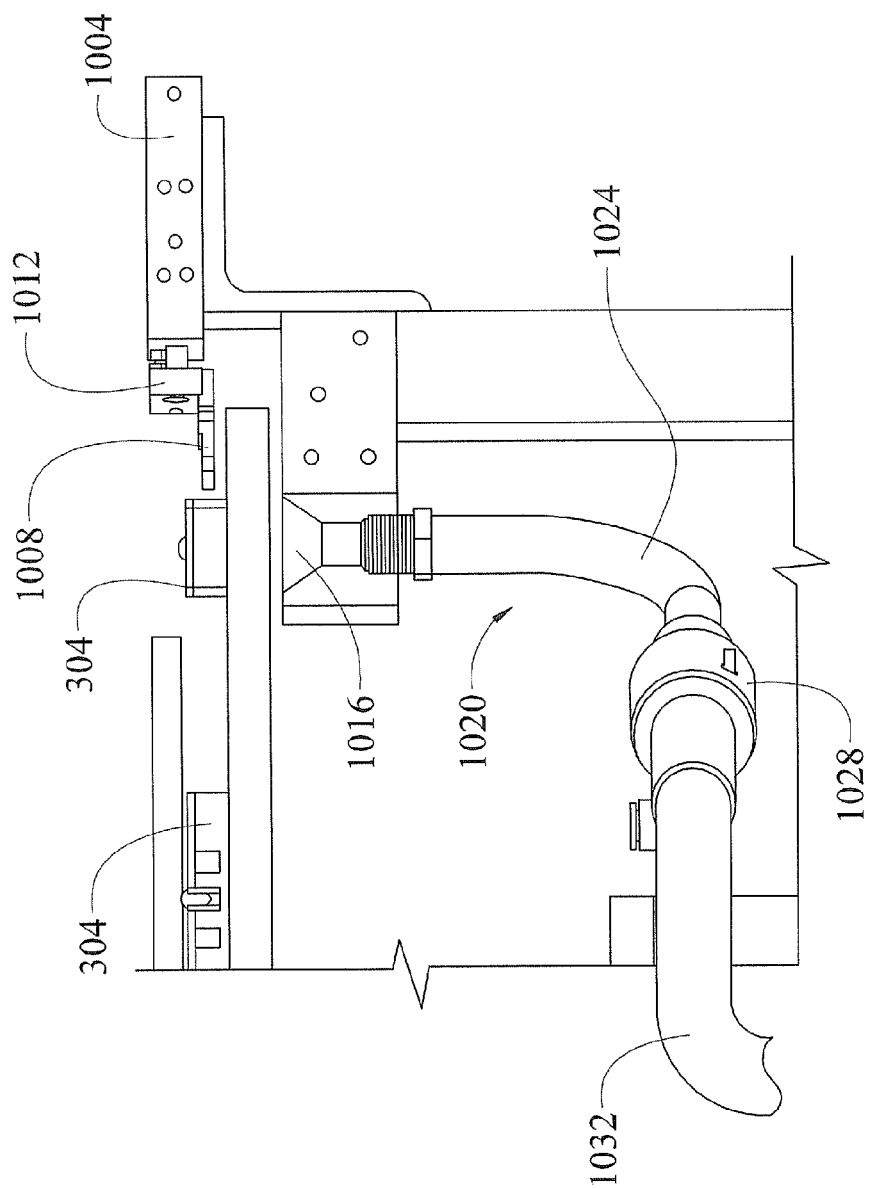
FIG. 15 is a side elevation view of a seed conveyor of the seed sampler system shown in FIG. 1, in accordance with various embodiments of the present disclosure.
Figure 16:
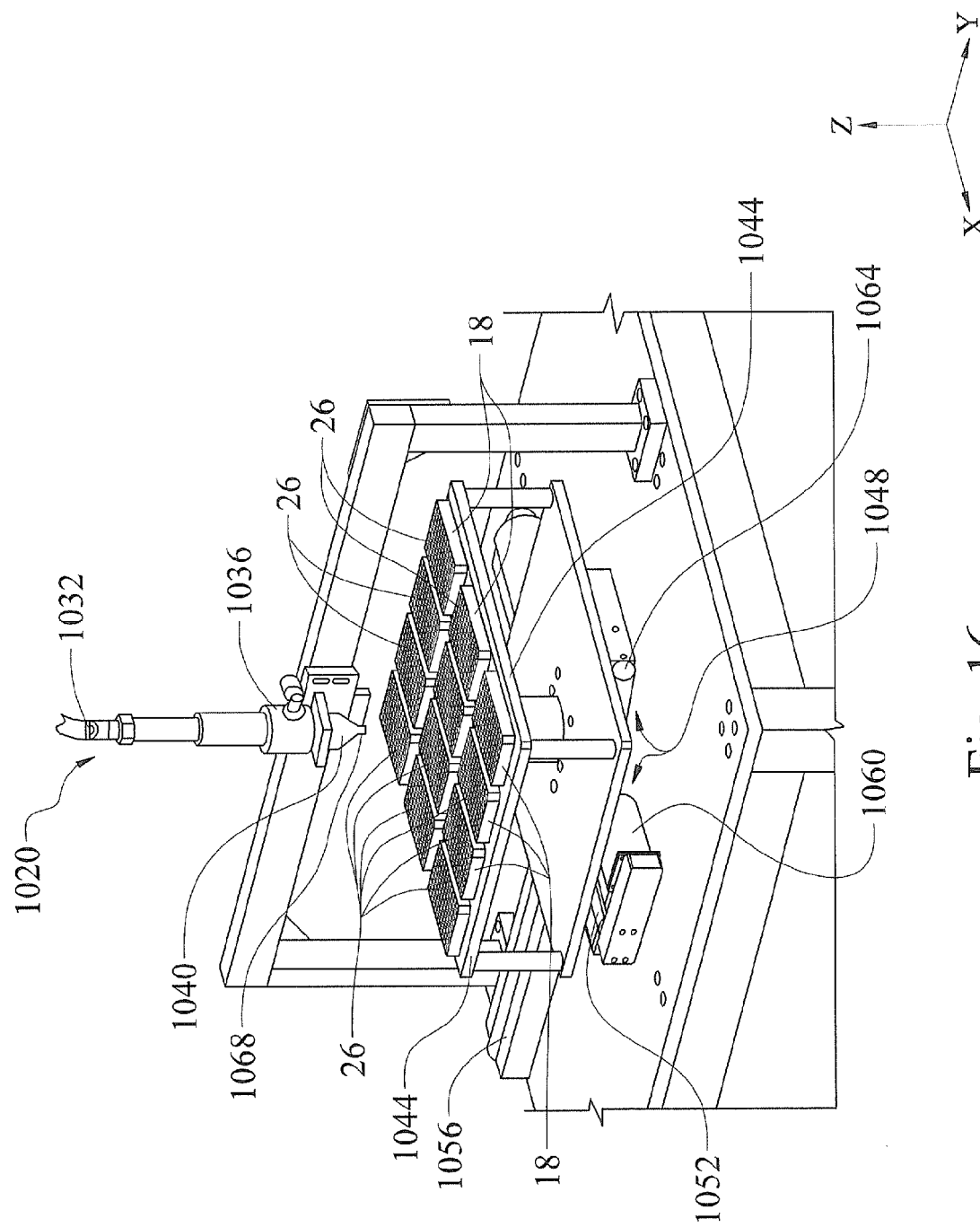
FIG. 16 is a perspective view of a seed tray platform of the seed sampler system shown in FIG. 1, in accordance with various embodiments of the present disclosure.

Referring now to FIGS. 15 and 16, after sampling and the optional seed treatment, the system controller advances the turntable 308 until the respective seed holder 304 is positioned adjacent a second clamp head spreader 1004 of the seed deposit subsystem 1000. The clamp head spreader 1004 is mounted to system support structure and includes a pair of fork tangs 1008 coupled to a fork base 1012. The clamp head spreader 1004 is substantially identical in form and function as the clamp head spreader 340 described above with reference to FIG. 5. Accordingly, upon activation of the clamp head spreader 1004, the fork base 1012 is extended toward the seed holder 304 such that the tangs 1008 are inserted into the fork passageways 336. As the tangs 1008 slide into the respective fork passageways 336, the clamp heads 312 of the respective seed holder 304 are retracted, as similarly described above. As the clamp heads 312 retract, the respective seed is allowed to fall through the coaxially aligned holes in the bottom of the seed holder seed channel 318 and the turntable 308 into a funnel 1016 of a seed conveyor 1020.

The seed conveyor 1020 comprises a first tube section 1024 coupled at a first end to the funnel 1016 and to an inlet of a first venturi device 1028 at a second end. A second tube section 1032 is connected at a first end to an outlet of the first venturi device 1028 and at a second end to an inlet of a second venturi device 1036. An outlet of the second venturi device 1036 is connected to seed dispenser 1040 that is mounted to system support structure above a seed tray platform 1044. The first venturi device 1028 is operable to induce an air flow in the first and second tube sections 1024 and 1032 toward the seed dispenser 1040. At the same time, the second venturi device 1036 is operable to induce an air flow toward the funnel 1016. Thus, the air flow induced by the first venturi device 1028 will draw the seed into the first funnel 1016 and first tube section 1020. Additionally, as the seed enters the first tube section 1024 it is propelled toward the seed dispenser 1040 by the air flow provided by the first venturi device 1028. Subsequently, as the seed nears the seed dispenser 1040, the seed is slowed down by the air flow provided by the second venturi device 1036 so that the seed is gently dispensed from the seed dispenser 1040, into a seed tray 18 without damaging the seed. In various embodiments, the air flow provided by the second venturi 1036 actually stops the movement of the seed, allowing the seed to drop under gravity into a seed tray 18. Various position sensors (not shown) can be provided on the first and second tube sections 1024 and 1032 to detect the presence of the seed, and provide input to the system controller to control operation of the seed conveyor 1020.

Referring particularly to FIG. 16, the seed deposit subsystem 1000 additionally includes a seed tray platform 1044 adapted to securely retain a plurality of seed trays 18 in fixed positions and orientations. Each seed tray 18 includes a plurality of seed wells 26, each of which are adapted for receiving a seed dispensed from the seed dispenser 1040. The seed dispenser 1040 is mounted to system support structure above the seed tray platform 1044 such that seeds can be dispensed from the seed dispenser 1040 into selected seed wells 26 of selected seed trays 18.

The seed tray platform 1044 is mounted to an X-Y stage 1048. The X-Y stage 1048 is a two-dimensional translation mechanism, including a first translating track 1052 and a second translating track 1056. The X-Y stage 1048 additionally includes a first linear actuator 1060 operable to bidirectionally move a first carriage (not shown) along the length of the first translating track 1052. The X-Y stage 1048 further includes a second linear actuator 1064 operable to bidirectionally move a second carriage (not shown) along the length of the second translating track 1056. The second translating track 1056 is mounted to the first carriage and the seed tray platform 1044 is mounted to the second carriage.

The first and second linear actuators 1060 and 1064 are controlled by the system controller to precisely move the seed tray platform 1044 in two dimensions. More particularly, the first and second actuators 1060 and 1064 move the seed tray platform 1044 within an X-Y coordinate system to precisely position any selected well 26 of any selected seed tray 18 at a target location beneath the seed dispenser 1040. The target location is the location in the X-Y coordinate system that is directly below a tip 1068 of the seed dispenser 1040. Once a seed holder 304 is positioned above the funnel 1016, the system controller positions a selected well 26, of a selected seed tray at the target location. The seed in the seed holder 304 is released into the funnel 1016 and transported to seed dispenser 1040, as described above, and gently deposited into the selected well.

As the seed trays 18 are placed on the seed tray platform 1044, a tray identification number, e.g., a bar code, for each seed tray 18 and the location of each seed tray 18 on the seed tray platform 1044 is recorded. Additionally, as each seed is deposited in a well 26, an X-Y location of the well, i.e., the target location, on the seed tray platform 1044 can be recorded. The recorded tray and well positions on the sample tray platform 1044 can then be compared to the X-Y locations of each deposited seed, to identify the specific seed in each well 26 of each seed tray 18.

As described above, each of the seed trays 18 and the sample trays 14 include a plurality of wells 26 and 22, respectively. In various embodiments, the number and arrangement of the wells 26 in the seed trays 18 corresponds to the number and arrangement of the wells 22 in the sample trays 14. This facilitates a one-to-one correspondence between a seed and its extracted sample. However, in some embodiments, it may be desirable to provide multiple wells 22 in the sample trays 14 for each well 26 in the seed trays 18, for example, where multiple tests may be run on the samples, or where different samples may be taken from the same seed (e.g. samples from different depths).

Referring now to FIG. 17, in various embodiments, the seed sampler system 10 additionally includes a collection tube loading station 1100 for mounting the collection tubes 624 on the tube mounts 616 of each CTP device 608. The tube loading station 1100 includes a hopper 1104 having a shaped surface and a vibrating feeder chute 1108 extending from an open bottom of the hopper 1104. Large amounts of collection tubes 624 can be deposited into the hopper 1104 where the vibrating feeder chute 1108 feeds the collection tubes 624 into a vibrating bowl feeder 1112. A gravity based feed track 1116 is connected to an outlet 1118 of the vibrating bowl feeder 1112 at a first end 1116A. A second end of the feed track 1116 terminates at a collection tube ram device 1120. The ram device 1120 extends orthogonally downward from the feed track second end 1116B and includes a longitudinal lift channel 1124 extending along the length of the ram device 1120. The ram device 1120 additionally includes a push mechanism (not shown) internal to the ram device 1120. The push mechanism can be any mechanism operable to push a collection tube 624, longitudinally positioned within the lift channel 1124, out an upper end 1120A of the ram device 1120. For example, the push mechanism can include a linear actuator that drives a ram shaped to receive at least a portion of a collection tube 624.

As the vibrating feeder bowl 1112 vibrates, collection tubes 624 migrate toward the outlet 1118 of the vibrating bowl feeder 1112. At the outlet 1118, the collection tubes 624 fall into the feed track first end 1116A that is shaped to cause the collection tubes 624 fall into a tube slot (not shown) that extends the length of the feed track 1116. More specifically, the collection tubes 624 are caused to fall tip-down into the tube slot and hang within the tube slot by a lip 620A of the collection tube base 620 (shown in FIG. 10). Gravity and vibration from the vibrating feeder bowl 1112 cause the collection tubes 624 to travel the length of the feed track 1116 and accumulate, single-file, at the feed track second end 1116B. As the collection tubes 624 accumulate, single-file at the second end 1116 the lead collection tube 624 will be longitudinally oriented within the longitudinal lift channel. The ram device 1120 is then actuated such that the push mechanism pushes the lead collection tube 624 out the upper end 1124A of the ram device lift channel 1124.

Prior to actuating the ram device 1120, the system controller will advance the rotating platform 604 to position a CTP device 608 above the second end 1116B of the feed track 1116. The system controller will further command the pivot bar actuator 632 to position the tube mount 616 in the load and deposit position, such that the tube mount distal end 618 is directly above the lift channel upper end 1124A. Therefore, as the lead collection tube is pushed, or lifted, out of the lift channel upper end 1124A the collection tube base 620 is pushed onto the tube mount distal end 618. The tube mount distal end 618 is sized such that there will be a friction fit between the collection tube base 620 and the tube mount distal end 618. Accordingly, the collection tube 624 is lifted out of the ram device 1120 and mounted on the respective tube mount. The next collection tube 624 in the feed track 1116 will then be positioned within the lift channel 1124 and a subsequent tube mount distal end 618 positioned to receive the collection tube 624.

Figure 18:
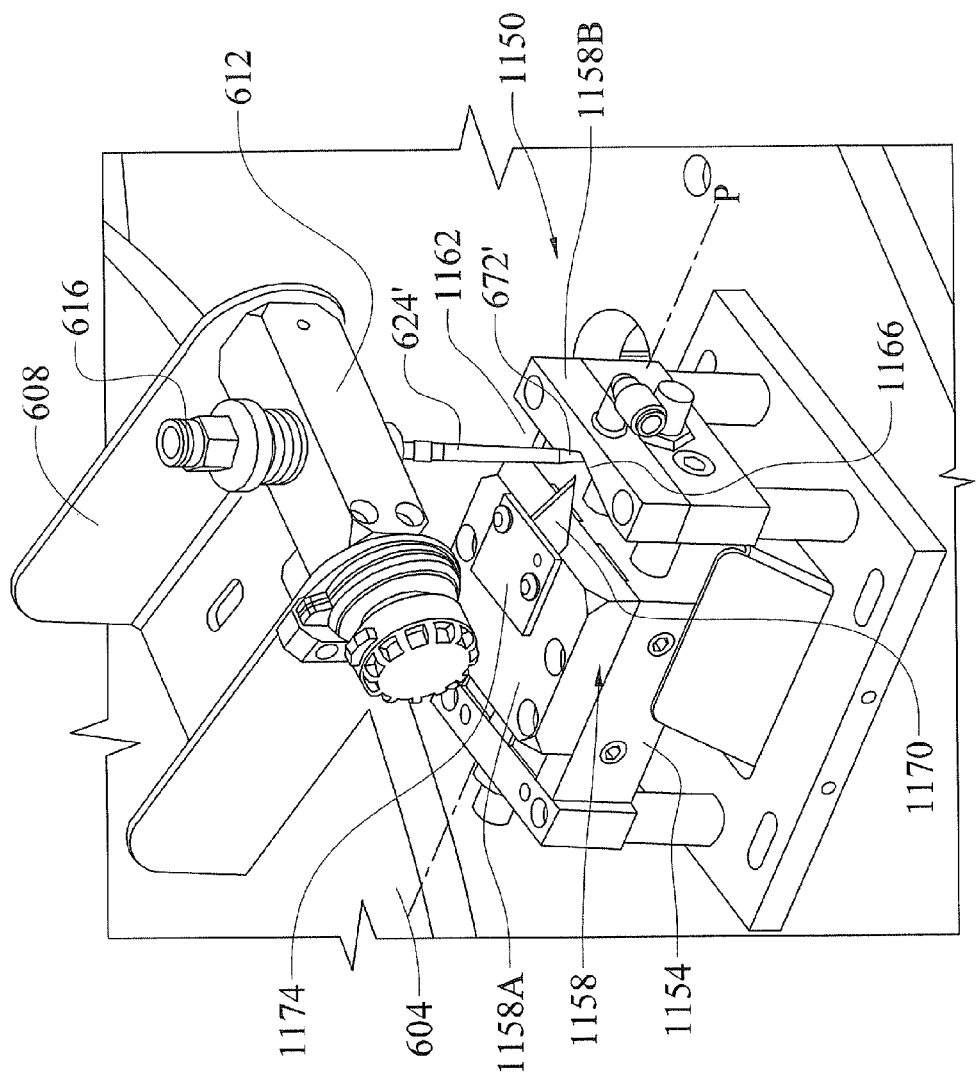
FIG. 18 is a perspective view of a collection tube preparation subsystem of the seed sampler system shown in FIG. 1, in accordance with various embodiments of the present disclosure.

Referring now to FIG. 18, in various embodiments, the collection tubes 624 can comprise commercially available pipettes, referred to herein as pipettes 624'. In such embodiments, the pipettes 624' may require a portion of the tip 672' be removed to allow for proper extraction of the sample, flushing of the pipette, and depositing of the aqueous sample in the sample trays 14. Therefore, in such embodiments, the seed sampler system 10 can include a collection tube preparation subsystem 1150 operable to cut off a portion of each pipette tip 672' after each pipette 624' has been mounted on a respective tube mount 616. The collection tube preparation subsystem 1150 includes a linear actuator 1154 operable to extend and retract a base 1158A of a cutter 1158 along a linear axis P. The linear actuator 1154 is mounted to system support structure below the rotating platform 604 such that when a newly mounted pipette 624', i.e., the pipette 624' has just been mounted on the respective tube mount 616, is advanced to the collection tube preparation subsystem 1150, the pipette tip 672' is positioned within a cutting chamber 1162.

The cutting chamber 1162 is formed between the cutter base 1158A and a cutting recess 1166 formed in a head 1158B of the cutter 1158. As illustrated in FIG. 18, when the newly mounted pipette 624' is advanced from the collection tube loading station 1100, the cutter base 1158A is in the retracted position and the tip 672' is positioned within the cutting recess 1166. Subsequently, the system controller commands the linear actuator 1154 to extend the cutter base 1158A. The cutter 1158 includes a cutting instrument 1170, e.g., a knife blade, fixedly coupled with, or held to, the cutter base 1158A by a cutting instrument bracket 1174. The cutting instrument is fixedly positioned such that when the linear actuator 1154 extends the cutter base 1158A, the cutting instrument will sever the pipette tip 672' thereby removing a portion of the tip 672'.

Figure 19:
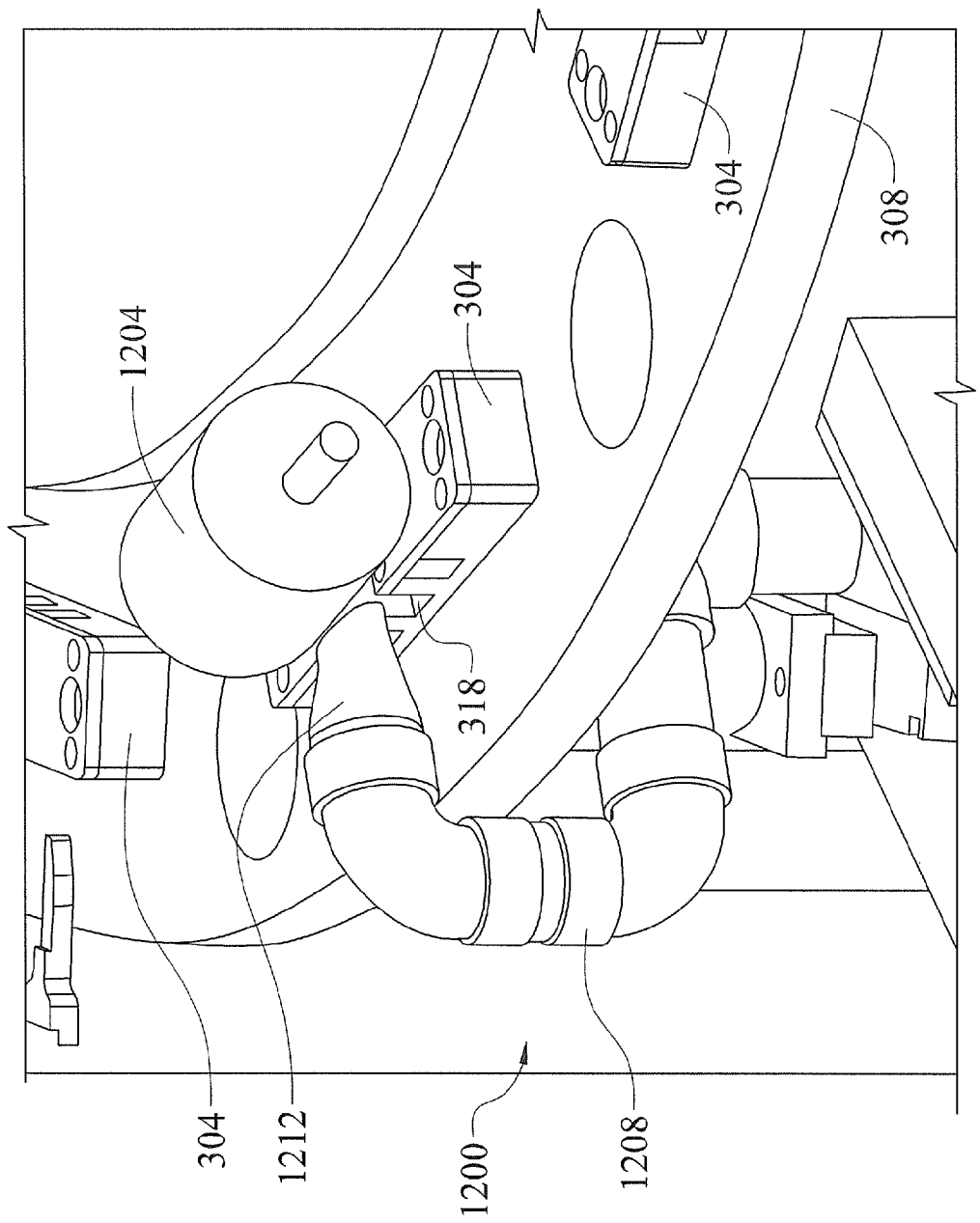
FIG. 19 is a perspective view of a cleaning station of the seed sampler system shown in FIG. 1, in accordance with various embodiments of the present disclosure.

Referring now to FIG. 19, in various embodiments, after the sampled seed has been deposited in a selected well 26 of a selected seed tray 18, the system controller advances the turntable 308 and positions the now empty seed holder 304 at a cleaning station 1200. The cleaning station 1120 is operable to clean and remove any residual seed sample and/or seed treatment, e.g., sealant, from the respective seed holder 304 after the sampled seed has been conveyed to a seed tray 18 and before a new seed is oriented and placed in the seed holder 304. The cleaning station comprises a roller brush 1204 and a vacuum 1208. The vacuum 1208 is connected to a vacuum source (not shown) to provide a vacuum at vacuum nozzle 1212 positioned in close proximity to the seed holder seed channel 318 when the respective seed holder 304 is advanced to the cleaning station 1200. The provided vacuum will remove any residual sample material and/or seed treatment that may have collected on the seed holder 304. Additionally, the roller brush 1204 is driven, e.g., electrically or pneumatically, to rotate on or with a roller shaft 1216. Simultaneous with providing the vacuum at the vacuum nozzle 1212, the system controller rotates the roller brush 1204 to remove any residual sample material and/or seed treatment that may have collected on the seed holder 304.

APPLICATIONS

The present disclosure provides methods for analyzing seeds having a desired trait, marker or genotype. In one aspect of the disclosure, the analytical methods allow individual seeds to be analyzed that are present in a batch or a bulk population of seeds such that the chemical and/or genetic characteristics of the individual seeds can be determined.

Samples prepared by the present disclosure can be used for determining a wide variety of physical, morphological, chemical and/or genetic traits. Generally, such traits are determined by screening the samples for one or more chemical or genetic characteristics indicative of the traits. Non-limiting examples of chemical characteristics include proteins, oils, starches, fatty acids, and metabolites. Accordingly, non-limiting examples of chemical traits include protein content, starch content, oil content, determination of fatty acid profiles, determination of metabolite profiles, etc. Genetic characteristics may include, for example, genetic markers, alleles of genetic markers, genes, DNA-derived sequences, RNA-derived sequences, promoters, quantative trait loci (QTL), 5'UTR, 3'UTR, satellite markers, transgenes, mRNA, ds mRNA, transcriptional profiles and methylation patterns.

In some embodiments, the methods and devices of the present disclosure can be used in a breeding program to select plants or seeds having a desired trait or marker genotype. The methods of the present disclosure can be used in combination with any breeding methodology and can be used to select a single generation or to select multiple generations. The choice of breeding method depends on the mode of plant reproduction, the heritability of the trait(s) being improved, and the type of cultivar used commercially (e.g., $F_1$ hybrid cultivar, pureline cultivar, etc.). Selected, non-limiting approaches for breeding the plants of the present disclosure are set forth below. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc., will generally dictate the choice.

In various embodiments, the methods of the present disclosure are used to determine the genetic characteristics of seeds in a marker-assisted breeding program. Such methods allow for improved marker-assisted breeding programs wherein nondestructive direct seed sampling can be conducted while maintaining the identity of individuals from the seed sampler to the field. As a result, the marker-assisted breeding program results in a "high-throughput" platform wherein a population of seeds having a desired trait, marker or genotype can be more effectively bulked in a shorter period of time, with less field and labor resources required. Such advantages will be more fully described below.

In other embodiments, the present disclosure provides a method for analyzing individual seeds within a population of seeds having genetic differences. The method comprises removing a sample comprising cells with DNA from seeds in the population without affecting the germination viability of the seeds; screening the DNA extracted from the sample for the presence or absence of at least one genetic marker; selecting seeds from the population based upon the results of the DNA screening; and cultivating plants from the selected seed.

As described above, the sampling systems and methods of this disclosure protect germination viability of the seeds so as to be non-destructive. Germination viability means that a predominant number of sampled seeds (i.e., greater than 50% of all sampled seeds) remain viable after sampling. In some particular embodiments, at least about 75% of sampled seeds, and in some embodiments at least about 85% of sampled seeds remain viable. It should be noted that lower rates of germination viability may be tolerable under certain circumstances or for certain applications, for example, as genotyping costs decrease with time because a greater number of seeds could be sampled for the same genotype cost.

In yet other embodiments, germination viability is maintained for at least about six months after sampling to ensure that the sampled seed will be viable until it reaches the field for planting. In some particular embodiments, the methods of the present disclosure further comprise treating the sampled seeds to maintain germination viability. Such treatment may generally include any means known in the art for protecting a seed from environmental conditions while in storage or transport. For example, in some embodiments, the sampled seeds may be treated with a polymer and/or a fungicide to protect the sampled seed while in storage or in transport to the field before planting.

In various embodiments, the samples of the present disclosure are used in a high-throughput, non-destructive method for analyzing individual seeds in a population of seeds. The method comprises removing a sample from the seed while preserving the germination viability of the seed; and screening the sample for the presence or absence of one or more characteristics indicative of a genetic or chemical trait. The method may further comprise selecting seeds from the population based on the results of the screening; and cultivating plants from the selected seed.

DNA may be extracted from the sample using any DNA extraction methods known to those of skill in the art which will provide sufficient DNA yield, DNA quality, and PCR response. A non-limiting example of suitable DNA-extraction methods is SDS-based extraction with centrifugation. In addition, the extracted DNA may be amplified after extraction using any amplification method known to those skilled in the art. For example, one suitable amplification method is the GenomiPhi® DNA amplification prep from Amersham Biosciences.

The extracted DNA is screened for the presence or absence of a suitable genetic marker. A wide variety of genetic markers are available and known to those of skill in the art. The DNA screening for the presence or absence of the genetic marker can be used for the selection of seeds in a breeding population. The screening may be used to select for QTL, alleles, or genomic regions (haplotypes). The alleles, QTL, or haplotypes to be selected for can be identified using newer techniques of molecular biology with modifications of classical breeding strategies.

In other various embodiments, the seed is selected based on the presence or absence of a genetic marker that is genetically linked with a QTL. Examples of QTLs which are often of interest include but are not limited to yield, lodging resistance, height, maturity, disease resistance, pest resistance, resistance to nutrient deficiency, grain composition, herbicide tolerance, fatty acid content, protein or carbohydrate metabolism, increased oil content, increased nutritional content, stress tolerance, organoleptic properties, morphological characteristics, other agronomic traits, traits for industrial uses, traits for improved consumer appeal, and a combination of traits as a multiple trait index. Alternatively, the seed can be selected based on the presence or absence of a marker that is genetically linked with a haplotype associated with a QTL. Examples of such QTL may again include, without limitation, yield, lodging resistance, height, maturity, disease resistance, pest resistance, resistance to nutrient deficiency, grain composition, herbicide tolerance, fatty acid content, protein or carbohydrate metabolism, increased oil content, increased nutritional content, stress tolerance, organoleptic properties, morphological characteristics, other agronomic traits, traits for industrial uses, traits for improved consumer appeal, and a combination of traits as a multiple trait index.

Selection of a breeding population could be initiated as early as the $F_2$ breeding level, if homozygous inbred parents are used in the initial breeding cross. An $F_1$ generation could also be sampled and advanced if one or more of the parents of the cross are heterozygous for the alleles or markers of interest. The breeder may screen an $F_2$ population to retrieve the marker genotype of every individual in the population. Initial population sizes, limited only by the number of available seeds for screening, can be adjusted to meet the desired probability of successfully identifying the desired number of individuals. See Sedcole, J. R. "Number of plants necessary to recover a trait." *Crop Sci.* 17:667-68 (1977). Accordingly, the probability of finding the desired genotype, the initial population size, and the targeted resulting population size can be modified for various breeding methodologies and inbreeding level of the sampled population.

The selected seeds may be bulked or kept separate depending on the breeding methodology and target. For example, when a breeder is screening an $F_2$ population for disease resistance, all individuals with the desired genotype may be bulked and planted in the breeding nursery. Conversely, if multiple QTL with varying effects for a trait such as grain yield are being selected from a given population, the breeder may keep individual identity preserved, going to the field to differentiate individuals with various combinations of the target QTL.

Several methods of preserving single seed identity can be used while transferring seed from the chipping lab to the field. Methods include, but are not limited to, transferring selected individuals to seed tape, a cassette tray, or indexing tray, transplanting with peat pots, and hand-planting from individual seed packets. Multiple cycles of selection can be utilized depending on breeding targets and genetic complexity.

The screening methods of the disclosure may further be used in a breeding program for introgressing a trait into a plant. Such methods comprise removing a sample comprising cells with DNA from seeds in a population, screening the DNA extracted from each seed for the presence or absence of at least one genetic marker, selecting seeds from the population based upon the results of the DNA screening; cultivating a fertile plant from the seed; and utilizing the fertile plant as either a female parent or male parent in a cross with another plant.

Examples of genetic screening to select seeds for trait integration include, without limitation, identification of high recurrent parent allele frequencies, tracking of transgenes of interest or screening for the absence of unwanted transgenes, selection of hybrid testing seed, and zygosity testing.

The identification of high recurrent pair allele frequencies via the screening methods of the present disclosure again allows for a reduced number of rows per population and an increased number of populations, or inbred lines, to be planted in a given field unit. Thus, the screening methods of the present disclosure may also effectively reduce the resources required to complete the conversion of inbred lines.

The methods of the present disclosure further provide quality assurance (QA) and quality control by assuring that regulated or unwanted transgenes are identified and discarded prior to planting.

The methods of the present disclosure may be further applied to identify hybrid seed for transgene testing. For example, in a conversion of an inbred line at the $BCnF_1$ stage, a breeder could effectively create a hybrid seed lot (barring gamete selection) that was 50% hemizygous for the trait of interest and 50% homozygous for the lack of the trait in order to generate hybrid seed for testing. The breeder could then screen all $F_1$ seeds produced in the test cross and identify and select those seeds that were hemizygous. Such method is advantageous in that inferences from the hybrid trials would represent commercial hybrid genetics with regard to trait zygosity.

Other applications of the screening methods of this disclosure for identifying and tracking traits of interest carry the same advantages identified above with respect to required field and labor resources. Generally, transgenic conversion programs are executed in multi-season locations which carry a much higher land and management cost structure. As such, the impact of either reducing the row needs per population or increasing the number of populations within a given field unit are significantly more dramatic on a cost basis versus temperate applications.

Still further, the screening methods of this disclosure may be used to improve the efficiency of the doubled haploid program through selection of desired genotypes at the haploid stage and identification of ploidy level to eliminate non-haploid seeds from being processed and advancing to the field. Both applications again result in the reduction of field resources per population and the capability to evaluate a larger number of populations within a given field unit.

In various embodiments, the disclosure further provides an assay for predicting embryo zygosity for a particular gene of interest (GOI). The assay predicts embryo zygosity based on the ratio of the relative copy numbers of a GOI and of an internal control (IC) gene per cell or per genome. Generally, this assay uses an IC gene that is of known zygosity, e.g., homozygous at the locus (two IC copies per diploid cell), for normalizing measurement of the GOI. The ratio of the relative copy numbers of the IC to the GOI predicts the GOI copy number in the cell. In a homozygous cell, for any given gene (or unique genetic sequence), the gene copy number is equal to the cell's ploidy level since the sequence is present at the same locus in all homologous chromosomes. When a cell is heterozygous for a particular gene, the gene copy number will be lower than the cell's ploidy level. The zygosity of a cell at any locus can thus be determined by the gene copy number in the cell.

In some particular embodiments, the disclosure provides an assay for predicting corn embryo zygosity. In corn seed, the endosperm tissue is triploid, whereas the embryo tissue is diploid. Endosperm that is homozygous for the IC will contain three IC copies. Endosperm GOI copy number can range from 0 (homozygous negative) to 3 (homozygous positive); and endosperm GOI copy number of 1 or 2 is found in seed heterozygous for the GOI (or hemizygous for the GOI if the GOI is a transgene). Endosperm copy number is reflective of the zygosity of the embryo: a homozygous (positive or negative) endosperm accompanies a homozygous embryo, heterozygous endosperm (whether a GOI copy number of 1 or 2) reflects a heterozygous (GOI copy number of 1) embryo. The endosperm GOI copy number (which can range from 0 to 3 copies) can be determined from the ratio of endosperm IC copy number to endosperm GOI copy number (which can range from 0/3 to 3/3, that is, from 0 to 1), which can then be used to predict zygosity of the embryo.

Copy numbers of the GOI or of the IC can be determined by any convenient assay technique for quantification of copy numbers, as is known in the art. Examples of suitable assays include, but are not limited to, Real Time (TaqMan®) PCR (Applied Biosystems, Foster City, Calif.) and Invader® (Third Wave Technologies, Madison, Wis.) assays. Preferably, such assays are developed in such a way that the amplification efficiency of both the IC and GOI sequences are equal or very similar. For example, in a Real Time TaqMan® PCR assay, the signal from a single-copy GOI (the source cell is determined to be heterozygous for the GOI) will be detected one amplification cycle later than the signal from a two-copy IC, because the amount of the GOI is half that of the IC. For the same heterozygous sample, an Invader® assay would measure a GOI/IC ratio of about 1:2 or 0.5. For a sample that is homozygous for both the GOI and the IC, the GOI signal would be detected at the same time as the IC signal (TaqMan®), and the Invader assay would measure a GOI/IC ratio of about 2:2 or 1.

These guidelines apply to any polyploid cell, or to haploid cells (such as pollen cells), since the copy number of the GOI or of the IC remain proportional to the genome copy number (or ploidy level) of the cell. Thus, these zygosity assays can be performed on triploid tissues such as corn endosperm.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. An automated seed sampler system, comprising:
    a milling station for removing at least a portion of seed coat material from a seed;
    a sampling station for extracting a sample of seed material from the seed where the seed coat has been removed;
    a seed transport subsystem for conveying the seed between the milling station and the sampling station; and
    a seed deposit subsystem for conveying the seed from the seed transport subsystem to a selected well in a seed tray after the seed has been sampled.

2. The system of claim 1, further comprising a sample collection and transport subsystem for capturing the extracted sample.

3. The system of claim 2, wherein the sample collection and transport subsystem includes a collection tube mounted on a collection tube placement device; and
    further comprising:
        a collection tube loading station for separating the collection tube from a plurality of like collection tubes and mounting the collection tube on the collection tube placement device; and
        a liquid delivery subsystem for delivering liquid to the collection tube to mix with the captured sample.

4. The system of claim 2, further comprising a sample deposit subsystem for conveying the captured sample from the sample collection and transport subsystem to a selected well in a sample tray.

5. The system of claim 1, further comprising a seed loading station for separating the seed from a plurality of like seeds in a bulk seed hopper.

6. The system of claim 5, further comprising an orientation system for receiving the seed from the seed loading station, orienting the seed in a desired orientation and conveying the oriented seed to a seed holder of the seed transport subsystem.

7. The system of claim 1, further comprising a seed treatment station for applying a seed treatment to at least the portion of the sampled seed having the seed coat removed, the seed treatment comprising at least one of a polymer and a fungicide sealer.

8. The system of claim 1, further comprising a cleaning station for removing residual sample material from a seed holder of the seed transport subsystem after the sample has been removed from the seed and the sampled seed has been conveyed to the selected well in the seed tray.

9. An automated seed sampler system, comprising:
    a milling station for removing at least a portion of seed coat material from a seed;
    a sampling station for extracting a sample of seed material from the seed where the seed coat has been removed;
    a sample collection and transport subsystem for capturing the extracted sample; and
    a sample deposit subsystem for conveying the captured sample from the sample collection and transport subsystem to a selected well in a sample tray.

10. The system of claim 9, wherein the sample collection and transport subsystem is configured to capture the extracted sample in a collection tube mounted on a collection tube placement device of the sample collection and transport subsystem; and
    further comprising:
        a collection tube loading station for separating the collection tube from a plurality of like collection tubes and mounting the collection tube on the collection tube placement device; and
        a liquid delivery subsystem for delivering liquid to the collection tube to mix with the captured sample.

11. The system of claim 10, wherein the sample deposit subsystem is operable to convey the mixed sample from the sample collection and transport subsystem to the selected well in the sample tray.

12. The system of claim 10, further comprising a collection tube discard station for removing the collection tube from the collection tube placement device and discarding the collection tube after the sample has been conveyed to the selected well of the sample tray.

13. The system of claim 10, further comprising:
    a seed transport subsystem for conveying the seed between the milling station and the sampling station; and a seed deposit subsystem for conveying the seed from the seed transport subsystem to a selected well in a seed tray after the seed has been sampled.

14. The system of claim 13, further comprising:
a seed loading station for separating the seed from a plurality of like seeds in a bulk seed hopper; and
an orientation system for receiving the seed from the seed loading station, orienting the seed in a desired orientation and conveying the oriented seed to a seed holder of the seed transport subsystem.

15. The system of claim 9, further comprising a seed treatment station for applying a seed treatment to at least the portion of the sampled seed having the seed coat removed.

16. An automated, high-throughput method for extracting sample material for testing from individual seeds in a population of seeds, the method comprising:
loading a seed in a seed holder of an automated seed sampler system;
removing at least a portion of seed coat material from the seed;
extracting a sample of seed material from the seed where the seed coat has been removed;
conveying the seed to a selected well in a seed tray after the seed has been sampled;
conveying the extracted sample to a selected well in a sample tray using a sample deposit subsystem of the seed sampler system; and
analyzing the extracted sample for one or more desired characteristics.

17. The method of claim 16, further comprising conveying the seed between a milling station where at least a portion of the seed coat material is removed from the seed and a sampling station where the sample of seed material is extracted from the seed where the seed coat has been removed using a seed transport subsystem.

18. The method of claim 17, wherein extracting the sample comprises:
capturing the extracted sample in a collection tube; and
delivering liquid to the collection tube to mix with the captured sample;
wherein conveying the extracted sample comprises conveying the mixed sample to a selected well in a sample tray.

19. The method of claim 17, wherein loading the seed comprises:
separating the seed from a plurality of like seeds in a bulk seed hopper;
orienting the seed in a desired orientation; and
conveying the oriented seed to the seed holder.

20. The method of claim 17, further comprising removing residual sample material from the seed holder after the sample has been removed from the seed and the sampled seed has been conveyed to the selected well in the seed tray.

21. The method of claim 20, further comprising applying a seed treatment to at least the portion of the sampled seed having the seed coat removed.

* * * * *